(12) United States Patent
Yang et al.

(10) Patent No.: US 10,646,139 B2
(45) Date of Patent: May 12, 2020

(54) BODY MOVEMENT TRACKING

(71) Applicant: Intel Corporation, Santa Clara, CA (US)

(72) Inventors: Xue Yang, San Jose, CA (US); Sheng Shen, Urbana, IL (US); Romit Roy Choudhury, Urbana, IL (US)

(73) Assignee: INTEL CORPORATION, Santa Clara, CA (US)

( * ) Notice: Subject to any disclaimer, the term of this patent is extended or adjusted under 35 U.S.C. 154(b) by 636 days.

(21) Appl. No.: 15/369,614

(22) Filed: Dec. 5, 2016

(65) Prior Publication Data

US 2018/0153444 A1    Jun. 7, 2018

(51) Int. Cl.
*A61B 5/11* (2006.01)
*A61B 5/00* (2006.01)

(52) U.S. Cl.
CPC .......... *A61B 5/1112* (2013.01); *A61B 5/0022* (2013.01); *A61B 5/1116* (2013.01); *A61B 5/1123* (2013.01); *A61B 5/725* (2013.01); *A61B 5/742* (2013.01)

(58) Field of Classification Search
CPC ... A61B 5/1112; A61B 5/0022; A61B 5/1116; A61B 5/1123; A61B 5/742; A61B 5/725
See application file for complete search history.

(56) References Cited

U.S. PATENT DOCUMENTS 7,953,246 B1    5/2011 Tu et al.
2013/0066815 A1*    3/2013 Oka .................. H04M 1/72569
                                                                706/12
2013/0244211 A1*    9/2013 Dowling ............. G06F 19/3481
                                                                434/247

(Continued)

FOREIGN PATENT DOCUMENTS

CN          103976739 A       8/2014

OTHER PUBLICATIONS

Attal, F., et al., "Physical Human Activity Recognition Using Wearable Sensors," Sensors (Basel) Dec. 2015; 15(12): 31314-31338. Published online Dec. 11, 2015. doi: 10.3390/s151229858, 25 pages.

(Continued)

*Primary Examiner* — Mohamed Charioui
*Assistant Examiner* — Eyob Hagos
(74) *Attorney, Agent, or Firm* — Schwabe, Williamson & Wyatt, P.C.

(57) ABSTRACT

Disclosed methods, systems, and storage media may track body movements and movement trajectories using internal measurement units (IMUs), where a first IMU may be attached to a first wrist of a user, a second IMU may be attached to a second wrist of the user, and a third IMU may be attached to a torso of the user. Upper body movements may be derived from sensor data produced by the three IMUs. IMUs are typically not used to detect fine levels of body movements and/or movement trajectory because most IMUs accumulate errors due to large amounts of measurement noise. Embodiments provide arm and torso movement models to which the sensor data is applied in order to derive the body movements and/or movement trajectory. Additionally, estimation errors may be mitigated using a hidden Markov Model (HMM) filter. Other embodiments may be described and/or claimed.

25 Claims, 7 Drawing Sheets

(56) References Cited

U.S. PATENT DOCUMENTS

2014/0276242 A1    9/2014    Chen et al.
2014/0371885 A1*  12/2014  Ianni .................. G06K 9/00342
                                                                 700/91
2015/0198995 A1*   7/2015  Muller .................. G06F 1/3221
                                                                  713/320
2016/0338621 A1*  11/2016  Kanchan ................ G16H 40/67

OTHER PUBLICATIONS

Rihar, A., et al., "Infant trunk posture and arm movement assessment using pressure mattress, inertial and magnetic measurement units (IMUs)," Journal of NeuroEngineering and Rehabilitation 2014, 11:133, <<retrieved from the Internet URL: https://jneuroengrehab.biomedcentral.com/articles/, DOI: 10.1186/1743-0003-11-133,>> 14 pages.

* cited by examiner

BODY MOVEMENT TRACKING

FIELD

The present disclosure relates to the field of movement tracking, and in particular, to apparatuses, methods and storage media for tracking body movements using wearable sensors.

BACKGROUND

The prevalence of smartphone and wearable device technologies has fueled an industry of health and fitness monitoring based on tracking biomechanical movements. Typically, motion sensors embedded in smartphones and/or wearable devices may be used to track relatively large movements, such as walking, running, biking, and the like. However, using motion sensors embedded in smartphones and/or wearable devices to track relatively small movements, such as arm, wrist, and/or hand movements, has proven to be more difficult.

Conventional techniques for tracking biomechanical movements use either computer vision (e.g., stereo, depth, and infrared cameras) or external localization systems (e.g., ultra-wideband (UWB) localization system, range radar, etc.). However, these systems usually require extensive hardware setups, and are typically only able to track movements within a predefined coverage area supported by the hardware setup. Additionally, these systems often suffer performance degradation from occlusion caused by the human body, occlusion caused by other objects, and/or environmental interference.

Some techniques for tracking biomechanical movements using motion sensors include applying various machine learning techniques to sensor data to identify certain activities, such as walking, running, cycling, etc. However, these machine learning techniques only identify a coarse semantic meaning of a particular activity, while a precise location trajectory of particular bodies/limbs involved in the identified activities is not known. Other techniques for tracking biomechanical movements using motion sensors generally require a plethora of motion sensors to be attached to multiple joints of a user. For example, many of these techniques require at least 7 inertial/magnetic sensors to track relative upper body motion. Using such a plethora of motion sensors may prove cumbersome and inhibit natural biomechanical movements.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

Figure 1:
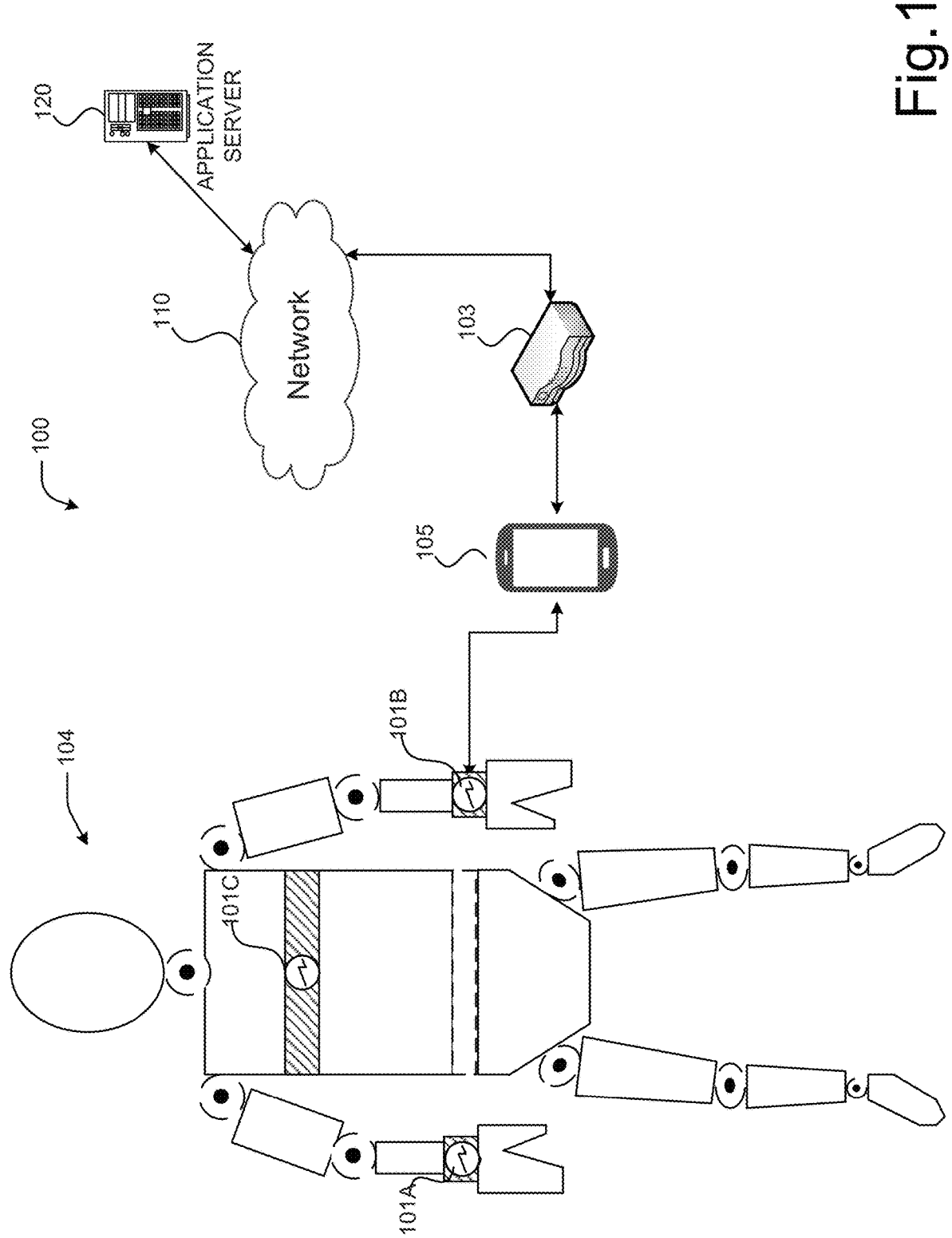
FIG. 1 illustrates an arrangement in which various example embodiments described in the present disclosure may be implemented.

Example embodiments are directed towards tracking body movements and movement trajectory using inertial measurement units (IMUs). In embodiments, the IMUs may comprise microelectromechanical systems (MEMS) including a 3-axis accelerometer, a 3-axis gyroscope, and a 3-axis magnometer. IMUs are typically not used to detect relatively fine levels of body movements and/or movement trajectory because most IMUs accumulate a large amount of errors due to large amounts of measurement noise. Embodiments provide that a first IMU may be attached to a first wrist of a user, a second IMU may be attached to a second wrist of the user, and a third IMU may be attached to a torso of the user. Some embodiments only utilize three IMU sensors (e.g., the afoementioned first, second, and third IMU sensors) without requiring any additional hardware elements, which greatly reduces complexity and costs as compared to existing solutions. In embodiments, various upper body movements are derived from sensor data produced by the three IMUs. By fusing the sensor data from the three IMU sensors, arm movements can be decoupled from body movements, which allows for arm movement tracking while the body is in motion and enables derivation of more precise upper body movements as compared to existing solutions. Embodiments provide an arm and torso movement model to which the sensor data may be applied in order to derive the fine level of body movements and/or movement trajectory. These motion models are used to track upper body movements including movement of both arms. Additionally, a hidden Markov Model (HMM) filter is used to allow for the effective tracking of arm placement/positions. In embodiments, estimation errors may be mitigated using (the HMM filter, given the limited search space of elbow and wrist joints. The embodiments herein have been shown to achieve a median tracking error of approximately 9 to 10 centimeters (cm) using only three IMUs and without any additional hardware requirements, which is a significant improvement over conventional motion tracking techniques.

In the following detailed description, reference is made to the accompanying drawings which form a part hereof wherein like numerals designate like parts throughout, and in which is shown by way of illustrated embodiments that may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

Various operations may be described as multiple discrete actions or operations in turn, in a manner that is most helpful in understanding the claimed subject matter. However, the order of description should not be construed to imply that the various operations are necessarily order-dependent. In particular, these operations might not be performed in the order of presentation. Operations described may be performed in a different order than the described embodiments. Various additional operations might be performed, or described operations might be omitted in additional embodiments.

The description may use the phrases "in an embodiment", "in an implementation", or in "embodiments" or "implementations", which may each refer to one or more of the same or different embodiments. Furthermore, the terms "comprising," "including," "having," and the like, as used with respect to embodiments of the present disclosure, are synonymous.

Also, it is noted that example embodiments may be described as a process depicted with a flowchart, a flow diagram, a data flow diagram, a structure diagram, or a block diagram. Although a flowchart may describe the operations as a sequential process, many of the operations may be performed in parallel, concurrently, or simultaneously. In addition, the order of the operations may be re-arranged. A process may be terminated when its operations are completed, but may also have additional steps not included in a figure. A process may correspond to a method, a function, a procedure, a subroutine, a subprogram, and the like. When a process corresponds to a function, its termination may correspond to a return of the function to the calling function a main function.

As disclosed herein, the term "memory" may represent one or more hardware devices for storing data, including random access memory (RAM), magnetic RAM, core memory, read only memory (ROM), magnetic disk storage mediums, optical storage mediums, flash memory devices or other machine readable mediums for storing data. The term "computer-readable medium" may include, but is not limited to, memory, portable or fixed storage devices, optical storage devices, and various other mediums capable of storing, containing or carrying instructions or data.

As used herein, the term "circuitry" refers to, is part of, or includes hardware components such as an Application Specific Integrated Circuit (ASIC), a field-programmable gate array (FPGA), programmable logic arrays (PLAs), complex programmable logic devices (CPLDs), one or more electronic circuits, one or more logic circuits, one or more processors (shared, dedicated, or group) and/or memory (shared, dedicated, or group) that are configured to provide the described functionality. In some embodiments, the circuitry may execute computer-executable instructions to provide at least some of the described functionality. The computer-executable instructions may represent program code or code segments, software or software logics, firmware, middleware or microcode, procedures, functions, subprograms, routines, subroutines, one or more software packages, classes, or any combination of instructions, data structures, program statements, and/or functional processes that perform particular tasks or implement particular data types. The computer-executable instructions discussed herein may be implemented using existing hardware in computer devices and communications networks.

As used herein, the term "network element," may be considered synonymous to or referred to as a networked computer, networking hardware, network equipment, router, switch, hub, bridge, gateway, or other like device. The term "network element" may describe a physical computer device of a network with wired or wireless communication links. The term "network element" may describe equipment that provides radio baseband functions for data or voice connectivity between a network and one or more users. The term "channel" as used herein may refer to any transmission medium, either tangible or intangible, which is used to communicate data or a data stream. The term "radio link" may be synonymous with and/or equivalent to "link," "channel," "communications tunnel," and/or any other like term denoting a pathway or medium through which data is communicated.

Referring now to the figures. FIG. 1 shows an arrangement 100 in accordance with various embodiments, suitable for practicing the present disclosure. As shown in FIG. 1, arrangement 100 may include a gateway (GW) 103, a computer device 105, network 110, application server 120, and computer devices 101A, 101B, and 101C (collectively referred to as "computer device 101" or "computer devices 101") affixed to a user 104 at least as shown by FIG. 1.

Computer devices 101, GW 103, and computer device 105 is capable of communicating using radio frequency (RF) signals. A computer device (such as computer device 105) is configured to determine in a global coordinate system (GCS), based on obtained sensor data, a right wrist acceleration and orientation based on first sensor data, a left wrist acceleration and orientation based on second sensor data, and a torso acceleration and orientation based on third sensor data; determine a relative acceleration of a right elbow (RARE) based on the right wrist and torso acceleration/orientation, and a relative acceleration of a left elbow (RALE) based on the left wrist and the torso acceleration/orientation; determine, using a hidden Markov Model filter (HMMF), a relative position of the right elbow (RPRE) or a relative position of the left elbow (RPLE) based on the RARE and the RALE; and control display of an avatar including a right arm position and orientation based on the RPRE and a left arm position and orientation based on the RPLE. These and other aspects of the teachings of the present disclosure will be described more fully infra.

Computer devices 101 may be IMUs or any device that is embedded with hardware that enable measurement and/or detection of motion, acceleration, rotation, and/or an orientation of the computer device 101. In embodiments, computer device 101 may include one or more MEMS or sensors, such as accelerometers, gyroscopes, magnetometers, and/or other like sensors. The one or more MEMS/sensors are configured to determine a magnitude and direction of a velocity, acceleration, and/or motion of the computer device 101, and convert the velocity, acceleration, and/or motion of the computer device 101 into position and/or orientation information. The changes in the positions and/or orientations of the computer device 101 may be indicative of a biomechanical motion performed by a user 104 of the computer device 101. The one or more sensors are configured to detect the biomechanical motion as sensor data. In various embodiments, the sensor data may include or otherwise indicate one or more spatial coordinates (or changes in spatial coordinates) for the positions and/or orientations of the computer device 101. The sensor data may then be passed to one or more processors and/or a sensor hub (e.g., sensor hub 250 as shown and described with regard to FIG. 2) of the computer device 101 to be converted into a biomechanical sequence, sensor coordinates, and/or any other type of format of analyzed, processed, or formatted data. Furthermore, the computer device 101 may track a timing of the biomechanical motion by timestamping the sensor data as it is collected and/or processed.

Computer devices 101 may also include hardware and/or software components that enable the computer device 101 to communicate with one or more other devices (e.g., computer device 105, GW 103, other computer devices 101, etc.) over a network (e.g., network 110) with little or no user intervention. In this regard, computer devices 101 may include a communications circuitry, such as a transmitter/receiver (or alternatively, a transceiver or RF circuitry), one or more memory devices, and one or more processors. To communicate with other devices, the computer device 101 may transmit and receive RF signals according to a wireless communications protocol. The wireless communications protocols may be any suitable set of standardized rules or instructions implemented by the computer device 101 to communicate with other devices. Examples of such wireless communications protocols may include, cellular communications protocols (e.g., Long Term Evolution (LTE), Universal Mobile Telecommunications System (UMTS), Global System for Mobile Communications (GSM) and/or Enhanced Data GSM Environment (EDGE), Wi-MAX or IEEE 802.16 protocols, and the like), Local Area Network (LAN), Wide Area Network (WAN), or wide LAN (WLAN) protocols (e.g., Wi-Fi-based protocols or Institute of Electrical and Electronics Engineers (IEEE) 802.11 protocols), and person-to-person (P2P) or personal area network (PAN) protocols (e.g., IEEE 802.15.4 based protocols including ZigBee, IPv6 over Low power Wireless Personal Area Networks (6LoWPAN), WirelessHART, MiWi, Thread, and the like; WiFi-direct; Bluetooth or Bluetooth Low Energy (BLE) protocols; ANT protocols; Z-Wave; LTE device-to-device (D2D) or Proximity Services (ProSe); Universal Plug and Play (UPnP); and the like). In some embodiments, the computer device 101 is embedded in a computer system and coupled with communications circuitry of the computer system. In embodiments where the computer device 101 is embedded in a computer system, such the computer device 101 may be a system on chip (SoC) or some other suitable system. The computer system may be a wearable computer device or wearable technology (e.g., a smart watch, fitness or activity tracker), a sensor system embedded in equipment (e.g., inside a baseball bat, a golf club, tennis racket, etc.), a telemetry system, or other like computer system.

Computer devices 101 are configured to capture and/or record data associated with an event. An event may be any occurrence of an action, such as reaching a velocity or acceleration threshold, a change in direction of a motion, a change in speed/velocity, a state/position/orientation change of the computer device 101, a temperature change, a change in biometric data (e.g., heartrate, etc.) or reaching a biometric threshold, and the like. In various embodiments, an event may be detected by computer device 101 based on sensor outputs, timer values, user actions, and the like. Once data associated with an event is captured and recorded by the computer device 101, the captured data may be provided to the computer device 105 (e.g., via a direct wireless connection). In some embodiments, the captured data may be relayed through the GW 103 and/or the network 110 and reported to a service provider (e.g., an operator of the application server 120) for processing and/or analysis.

The computer devices 101 are configured to capture or record sensor data based on a desired event or trigger and report the captured/recorded sensor data based on another event or trigger. For example, in some embodiments, the computer devices 101 may begin recording sensor data when the computer device 101 detects a first signal from a button or touchscreen input, and may stop recording sensor data when the computer device 101 has detected a second signal from the button or touchscreen input. In another embodiment, the computer devices 101 may begin recording sensor data when the computer devices 101 detect that a velocity threshold has been reached and may stop recording sensor data when the computer devices 101 have fallen below the velocity threshold. Further, the computer device 101 may report the recorded sensor data once the computer device 101 has fallen below the velocity threshold. In another embodiment, the computer devices 101 may begin recording sensor data when a communications session is established with the computer device 105 and may stop recording sensor data when the communications session ends or terminates. In embodiments, the computer device 101 may report recorded sensor data on a periodic basis. In such embodiments, the computer device 105 may determine or identify portions of the sensor data to be used for biomechanical analysis.

Computer device 105 is a physical hardware device or collection of hardware elements that is/are capable of running or executing one or more applications. Computer device 105 may include a transmitter/receiver (or alternatively, a transceiver or RF circuitry), memory, one or more processors, one or more sensors (e.g., accelerometers, gyroscopes, image sensors, Global Positioning System (GPS) receiver, proximity sensors, etc.), and/or other like components. Computer device 105 may communicate (transmit/receive) data with computer device 101, and communicate data with application server 120 via network 110 and/or GW 103. Computer device 105 may communicate with the application server 120 via the network 110 and/or GW 103 in accordance with one or more wireless or wired communications protocols as discussed herein. Computer device 105 may communicate with computer devices 101 in accordance with one or more wireless communications protocols as discussed herein. Computer device 105 is configured to run, execute, or otherwise operate one or more applications for generating simulations of biomechanical motions, which may include for example, operating the biomechanical feedback generation/display processes of the example embodiments (e.g., process 600 as shown and described with regard to FIG. 6). These applications may be native applications, web applications, and/or hybrid applications. Computer device 105 may be a wireless cellular phone, a smartphone, a laptop personal computer (PCs), a tablet PC, a handheld messaging device, a personal data assistant, an electronic book reader, an augmented reality head-mounted (or helmet-mounted) display device, a network-enabled television (e.g., a "smart TV"), and/or any other physical or logical device capable of recording, storing, and/or transferring digital data. As such, the computer device 105 is capable of establishing a radio link with each of the computer devices 101 according to one or more of the previously mentioned wireless communications protocols to obtain sensor data captured by the computer device 101.

GW 103 is a network element that employs multi-radio frequency networks technology, and may provide network connectivity for the computer device 105 and/or the computer device 101. In this regard, the GW 103 may also communicate data to/from the application server 120 via the network 110 on behalf of the Computer device 101 and/or computer device 105. Further, GW 103 may act as a single point of contact between devices that are unable to directly connect to larger networks (e.g., network 110) and remote computer devices. In such embodiments, GW 103 may be a wireless access point (WAP), a home server coupled with RF communications logic, a smallcell base station (e.g., a femtocell, picocell, home evolved nodeB (HeNB), and the like), a router, a switch, a hub, a radio beacon, and/or any other like device that may provide network connectivity to the elements in arrangement 100. In some embodiments, the GW 103 may be communicatively coupled with a WAP through a wired or wireless connection. The GW 103 may include one or more processors, communications circuitry (e.g., including a network interface, one or more transmitters/receivers connected to one or more antennas, and the like), and computer readable media. The one or more transmitters/receivers (or transceivers) are configured to wirelessly transmit/receive RF signals to/from computer device 101 and/or computer device 105, and the network interface is configured to transmit/receive data to/from application server 120 via network 110 using a wired connection. The GW 103 may process and/or route data packets over the wired connection according to one or more communications protocols, such as Ethernet (e.g., IEEE 802.1, 802.2, and 802.3 protocols); Point-to-Point Protocol (PPP) over Ethernet (PPPoE); PPP over asynchronous transfer mode (ATM) (PPPoA); High Level Data Link Control (HDLC); and/or any other like protocols. In embodiments where multiple computer devices 101 are employed (e.g., when a user uses multiple wearable devices, when an environment includes multiple users using one or more wearable devices, etc.), GW 103 may provide communication services to computer device 105 and/or computer device 101 by coordinating communications between the multiple computer devices 101 and the computer device 105. In this regard, the GW 103 may act as a centralized hub and/or scheduler for the various devices. In some embodiments, the GW 103 may be a standalone device that is specifically manufactured to provide computer device 101 and/or computer device 105 with connectivity to network 110, such as an Internet of Things (IoT) GW, an automation hub, or some other suitable device. In this regard, GW 103 may be used in deployment scenarios where multiple computer devices 101 are employed, such as a gym or training center with multiple users and/or computer devices 101/105.

Network 110 may be any network that allows computers to exchange data. Network 110 may include one or more network elements (not shown) capable of physically or logically connecting computers. The network 110 may include any appropriate network, including an intranet, the Internet, a cellular network, a local area network (LAN) or wireless LAN (WLAN), a personal network, an enterprise network, or any other such network or combination thereof. Components used for such a system can depend at least in part upon the type of network and/or environment selected. Protocols and components for communicating via such a network are well known and will not be discussed herein in detail. Communication over the network may be enabled by wired or wireless connections, and combinations thereof.

Application server 120 may include one or more systems and/or applications for providing one or more services to one or more clients (e.g., computer device 105). Application server 120 may include one or more processors, memory or computer readable storage media, a network interface, and/or other like components. Additionally, application server 120 may be a single physical hardware device, or may be physically or logically connected with other network devices and/or data storage devices, and/or operate as or within a cloud computing service. Application server 120 may be connected to, or otherwise associated with one or more data storage devices (not shown). The application server 120 is any device capable of receiving and responding to requests from one or more client devices (e.g., computer device 105 or computer device 101) across a computer network (e.g., network 110) to provide one or more services. The application server 120 may include an operating system that may provide executable program instructions for the general administration and operation of application server 120, and may include a computer-readable medium storing instructions that, when executed by a processor of the application server 120, may allow the application server 120 to perform its intended functions. Suitable implementations for the operating system and general functionality of the servers are known or commercially available, and are readily implemented by persons having ordinary skill in the art, particularly in light of the disclosure herein. Furthermore, it should be understood that the application server 120 may not be required and the applications and software components discussed herein may be executed on any appropriate device or host machine.

In some embodiments, the application server 120 may provide IoT device services that may utilize information obtained/recorded by the computer device 101. For example, in some embodiments the application server 120 may perform the biomechanical analysis/tracking processes of the example embodiments. In other embodiments, the computer device 105 may perform the biomechanical analysis/tracking processes of the example embodiments, and the application server 120 may provide additional or supplementary services, such as athletic performance analytics and analysis based on results of the biomechanical analysis/tracking provided by the computer device 105. The application server 120 may obtain sensor data from the computer devices 101 or biomechanical analysis/tracking data from the computer device 105, analyze such data, and may be able to generate content such as text, graphics, audio and/or video to be transferred to computer device 105, via a web server (not shown) in the form of HTML, XML, ASP, MPEG-DASH, Java™, JSP, PHP, and/or any other appropriate structured language or server-side scripting language. The handling of requests and responses, (e.g., requests for information/content and the information/content provided in response) may be handled by the web server (not shown).

The user 104 may be an operator of a system including at least the computer devices 101 and the computer device 105. In various embodiments, the user 104 may affix or couple the computer devices 101 to his/her body. As shown, computer device 101A may be coupled with a right wrist of the user 104, computer device 101B may be coupled with a left wrist of the user 104, and computer device 101C may be coupled with a torso of the user 104. Sensor data captured by the computer devices 101 may be used to determine a position and/or orientation (PO) of at least the upper body motions of the user 104.

In FIG. 1, only three computer devices 101, one GW 103, one computer device 105, and a single application server 120 are shown. According to various embodiments, any number of wearable devices or sensors, any number of GWs, any number of client devices, any number of servers, and/or any number of databases (not shown) may be present. Additionally, in some embodiments, application server 120 and/or one or more associated databases (not shown) may be virtual machines, and/or they may be provided as part of a cloud computing service. In various embodiments, application server 120 and one or more databases may reside on one physical hardware device, and/or may be otherwise fully integrated with one another. Thus, the depiction of the illustrative arrangement 100 in FIG. 1 should be taken as being illustrative in nature, and not limited to the scope of the disclosure.

Figure 2:
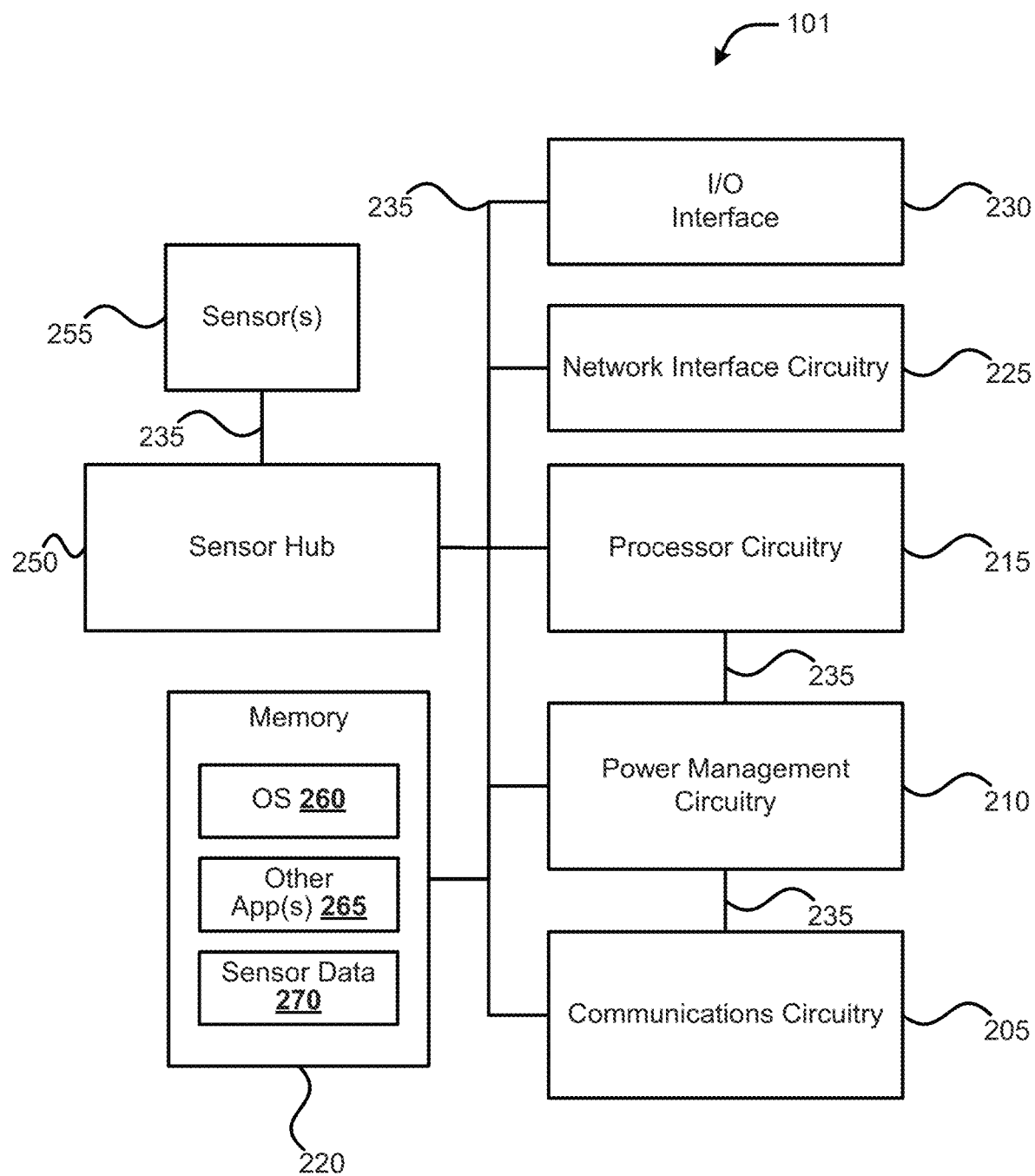
FIG. 2 illustrates the components of a computer device in accordance with various example embodiments in accordance with various example embodiments.

FIG. 2 illustrates the components of a computer device 101, in accordance with various example embodiments. In embodiments, computer device 101 may comprise communications circuitry 205, power management circuitry (PMC) 210, processor circuitry 215, memory 220 (also referred to as "computer-readable media 220" or "CRM 220"), network interface circuitry (NIC) 225, input/output (I/O) interface 230, one or more sensors 255 (also referred to as "sensor(s)

255"), and sensor hub 250, coupled with each other by bus 235 at least as shown by FIG. 2.

CRM 220 is a hardware device configured to store an operating system (OS) 260 and program code for one or more software components, such as sensor data 270 and/or one or more other application(s) 265. CRM 220 is a computer readable storage medium that may generally include a volatile memory (e.g., random access memory (RAM), synchronous dynamic RAM (SDRAM) devices, double-data rate synchronous dynamic RAM (DDR SDRAM) device, flash memory, and the like), non-volatile memory (e.g., read only memory (ROM), solid state storage (SSS), non-volatile RAM (NVRAM), and the like), and/or other like storage media capable of storing and recording data. Instructions, program code and/or software components are loaded into CRM 220 by one or more network elements via network 110 and communications circuitry 205 using over-the-air (OTA) interfaces or via NIC 225 using wired communications interfaces (e.g., from application server 120, a remote provisioning service, etc.). In some embodiments, software components are loaded into CRM 220 during manufacture of the computer device 101, or loaded from a separate computer readable storage medium into memory 220 using a drive mechanism (not shown), such as a memory card, memory stick, removable flash drive, removable sim card, a secure digital (SD) card, and/or other like computer readable storage medium (not shown).

During operation, memory 220 may include OS 260, sensor data 270, and other application(s) 265. OS 260 may manage computer hardware and software resources and provide common services for computer programs. OS 260 may include one or more drivers or application programming interfaces (APIs) that provide an interface to hardware devices thereby enabling OS 260 and other application(s) 265 to access hardware functions without needing to know the details of the hardware itself. The OS 260 may be a general purpose operating system or an operating system specifically written for and tailored to the computer device 101. Sensor data 270 is a collection of data based on measurements obtained by the one or more sensor(s) 255 and processed by sensor hub 250. In embodiments, the sensor data 270 may include component parts that correspond to a particular sensor 255, such as a gyroscope component that corresponds to data captured by a gyroscope, an acceleration component that corresponds to data captured by an accelerometer, a magnetization component that corresponds to data captured by a magnetometer, and other components that correspond to data captured by other sensors. The acceleration component may indicate an acceleration along three axes (including acceleration due to gravity) as measured by the accelerometer, the gyroscopic component may indicate an angular velocity around three axes as measured by the gyroscope, and the magnetization component may indicate a magnetic field along the three axes as measured by the magnetometer. Other application(s) 265 may be a collection of logic and/or program code that enables the computer device 101 to perform various other functions of the computer device 101.

Processor circuitry 215 is configured to carry out instructions of a computer program by performing the basic arithmetical, logical, and input/output operations of the system. The processor circuitry 215 may include one or more processors (e.g., a single-core processor, a dual-core processor, a triple-core processor, a quad-core processor, etc.), one or more microcontrollers, one or more digital signal processors (DSPs), FPGAs (hardware accelerators), and the like. In embodiments, the processor circuitry 215 may include feature-matching capabilities that allows the processor circuitry 215 to recognize patterns of incoming sensor data 270 from the sensor hub 250. In addition, the processor circuitry 215 is capable of controlling the storage of sensor data 270 in memory 220. The processor circuitry 215 may perform the aforementioned functions, process data, and perform a variety of other functions for the computer device 101 by executing program code, logic or software modules, firmware, middleware, microcode, hardware description languages, and/or any other like set of instructions stored in the memory 220. The program code may be provided to processor circuitry 215 by memory 220 via bus 235 and/or via communications circuitry 205, NIC 230, or separate drive mechanism. On execution of the program code by the processor circuitry 215, the processor circuitry 215 may cause computer device 101 to perform the various operations and functions delineated by the program code, such as the various example embodiments discussed herein. In embodiments where processor circuitry 215 includes (FPGA based) hardware accelerators as well as processor cores, the hardware accelerators (e.g., the FPGA cells) may be pre-configured (e.g., with appropriate bit streams) with the logic to perform some of the functions of OS 260 and/or other applications 265 (in lieu of employment of programming instructions to be executed by the processor core(s)).

Sensor(s) 255 include any device or devices that are capable of converting a mechanical motion into an electrical signal, such as one or more MEMS with piezoelectric, piezoresistive and/or capacitive components, which may be used to determine environmental conditions or location information related to the computer device 101. In embodiments, the one or more MEMS may include one or more 3-axis accelerometers, one or more 3-axis gyroscopes, and one or more magnetometers. In some embodiments, the sensors 255 may also include one or more gravimeters, altimeters, barometers, proximity sensors (e.g., infrared radiation detector and the like), depth sensors, ambient light sensors, thermal sensors, ultrasonic transceivers, and/or positioning circuitry. The positioning circuitry may also be part of, or interact with, the communications circuitry 205 to communicate with components of a positioning network, such as a Global Navigation Satellite System (GNSS) and/or a Global Positioning System (GPS). In some embodiments, the positioning circuitry may be a Micro-Technology for Positioning, Navigation, and Timing (Micro-PNT) integrated circuit (IC) that uses a master timing clock to perform position tracking/estimation without GNSS and/or GPS.

Sensor hub 250 may act as a coprocessor for processor circuitry 215 by processing data obtained from the sensor(s) 255. The sensor hub 250 may include one or more processors (e.g., a single-core processor, a dual-core processor, a triple-core processor, a quad-core processor, etc.), one or more microcontrollers, one or more DSPs, FPGAs (hardware accelerators), and/or other like devices. Sensor hub 250 is configured to integrate data obtained from each of the sensor(s) 255 by performing arithmetical, logical, and input/output operations. In embodiments, the sensor hub 250 may capable of timestamping obtained sensor data, provide sensor data to the processor circuitry 215 in response to a query for such data, buffering sensor data, continuously streaming sensor data to the processor circuitry 215 including independent streams for each sensor 255 (e.g., where the sensor(s) 255 includes multiple MEMs), reporting sensor data based upon predefined thresholds or conditions/triggers, and/or other like data processing functions.

PMC 210 is an integrated circuit (e.g., a power management integrated circuit (PMIC)) or a system block in a system on chip (SoC) used for managing power requirements of the computer device 101. The power management functions may include power conversion (e.g., alternating current (AC) to direct current (DC), DC to DC, etc.), battery charging, voltage scaling, and the like. PMC 210 may also communicate battery information to the processor circuitry 215 when queried. The battery information may indicate whether the computer device 101 is connected to a power source, whether the connected power sources is wired or wireless, whether the connected power sources is an alternating current charger or a USB charger, a current voltage of the battery, a remaining battery capacity as an integer percentage of total capacity (with or without a fractional part), a battery capacity in microampere-hours, an average battery current in microamperes, an instantaneous battery current in microamperes, a remaining energy in nanowatt-hours, whether the battery is overheated, cold, dead, or has an unspecified failure, and the like. PMC 210 may be communicatively coupled with a battery or other power source of the computer device 101 (e.g., nickel-cadmium (NiCd) cells, nickel-zinc (NiZn) cells, nickel metal hydride (NiMH) cells, and lithium-ion (Li-ion) cells, a supercapacitor device, an ultracapacitor device, a fuel cell device, etc.).

NIC 225 is a computer hardware component that connects computer device 101 to a computer network via a wired connection. To this end, NIC 225 may include one or more ports and one or more dedicated processors and/or FPGAs to communicate using one or more wired network communications protocol, such as Ethernet, token ring, Fiber Distributed Data Interface (FDDI), Point-to-Point Protocol (PPP), and/or other like network communications protocols). The NIC 225 may also include one or more virtual network interfaces configured to operate with the one or more applications of the computer device 101.

I/O interface 230 is a computer hardware component that provides communication between the computer device 101 and one or more other devices. The I/O interface 230 may include one or more user interfaces designed to enable user interaction with the computer device 101 and/or peripheral component interfaces designed to provide interaction between the computer device 101 and one or more peripheral components. User interfaces may include, but are not limited to a physical keyboard or keypad, a touchpad, a speaker, a microphone, etc. Peripheral component interfaces may include, but not limited to, a non-volatile memory port, an audio jack, a power supply interface, a serial communications protocol (e.g., Universal Serial Bus (USB), FireWire, Serial Digital Interface (SDI), and/or other like serial communications protocols), a parallel communications protocol (e.g., IEEE 1284, Computer Automated Measurement And Control (CAMAC), and/or other like parallel communications protocols), etc.

Bus 235 is configured to enable the communication and data transfer between processor circuitry 215 and memory 220. Bus 235 may comprise a high-speed serial bus, parallel bus, internal universal serial bus (USB), Front-Side-Bus (FSB), a PCI bus, a PCI-Express (PCI-e) bus, a Small Computer System Interface (SCSI) bus, an SCSI parallel interface (SPI) bus, an Inter-Integrated Circuit (I2C) bus, a universal asynchronous receiver/transmitter (UART) bus, and/or any other suitable communication technology for transferring data between components within computer device 101.

Communications circuitry 205 includes circuitry for communicating with a wireless network and/or cellular network. Communications circuitry 205 is used to establish a networking layer tunnel through which the computer device 101 may communicate with other computer devices. Communications circuitry 205 may include one or more processors (e.g., baseband processors, etc.) that are dedicated to a particular wireless communication protocol (e.g., Wi-Fi and/or IEEE 802.11 protocols), a cellular communication protocol (e.g., Long Term Evolution (LTE) and the like), and/or a wireless personal area network (WPAN) protocol (e.g., IEEE 802.15.4-802.15.5 protocols including ZigBee, WirelessHART, 6LoWPAN, etc.; or Bluetooth or Bluetooth low energy (BLE) and the like). The communications circuitry 205 may also include hardware devices that enable communication with wireless networks and/or other computer devices using modulated electromagnetic radiation through a non-solid medium. Such hardware devices may include switches, filters, amplifiers, antenna elements, and the like to facilitate the communication over-the-air (OTA) by generating or otherwise producing radio waves to transmit data to one or more other devices via the one or more antenna elements, and converting received signals from a modulated radio wave into usable information, such as digital data, which may be provided to one or more other components of computer device 105 via bus 335.

In some embodiments, the components of computer device 101 may be packaged together to form a single package, IC, or SoC. For example, in some embodiments the PMC 210, processor circuitry 215, memory 220, and sensor hub 250 may be included in an SoC that is communicatively coupled with the other components of the computer device 101. Additionally, although FIG. 2 illustrates various components of the computer device 101, in some embodiments, computer device 101 may include more or less components than those shown in FIG. 2.

Figure 3:
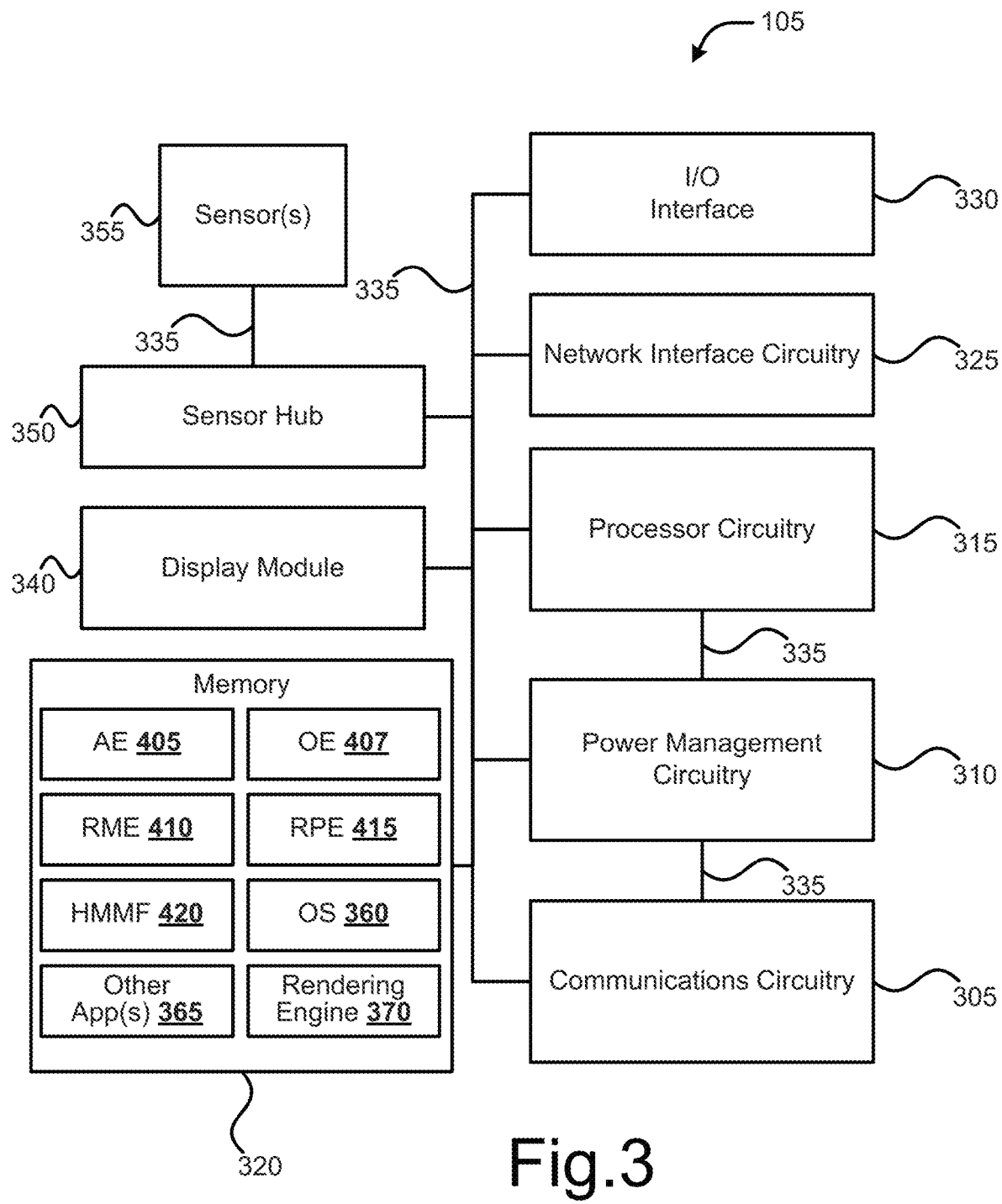
FIG. 3 illustrates the components of another computer device in accordance with various example embodiments.

FIG. 3 illustrates the components of a computer device 105, in accordance with various example embodiments. In embodiments, computer device 105 may comprise communications circuitry 305, PMC 310, processor circuitry 315, memory 320 (also referred to as "computer-readable media 320" or "CRM 320"), NIC 330, I/O interface 335, display module 340, sensor hub 350, and one or more sensors 355 (also referred to as "sensor(s) 355") coupled with each other by bus 335 at least as shown by FIG. 3. In embodiments, the components of computer device 105 may be the same or similar to the components of computer device 101 discussed previously. For example, communications circuitry 305 may be the same or similar as communications circuitry 205, PMC 310 may be the same or similar as PMC 210, processor circuitry 315 may be the same or similar as processor circuitry 215, CRM 320 may be the same or similar as CRM 220, NIC 325 may be the same or similar as NIC 225, I/O interface 330 may be the same or similar as I/O interface 230, bus 335 may be the same or similar as bus 235, sensor hub 350 may be the same or similar as sensor hub 250, and sensor(s) 355 may be the same or similar as sensor(s) 255. For the sake of brevity, only the differences between the components of computer device 105 and the components of computer device 101 will be discussed infra.

CRM 320 may be the same or similar as CRM 220, but during operation, CRM 320 may store program code for OS 360, other application(s) 365, rendering engine 370, acceleration engine (AE) 405, orientation engine (OE) 407, relative motion engine (RME) 410, relative position engine (RPE) 415, and hidden Markov Model filter (HMMF) 420. OS 360 may manage computer hardware and software resources and provide common services for computer programs. OS 360 may include one or more drivers or application APIs that provide an interface to hardware devices thereby enabling OS 360 and the aforementioned modules to access hardware functions without needing to know the details of the hardware itself. The AE 405, OE 407, RME 410, RPE 415, and HMMF 420 may use the drivers and/or APIs to obtain data/information from other components/sensors 355 of the computer device 105 to perform their respective functions. The OS 360 may be a general purpose operating system or an operating system specifically written for and tailored to the computer device 105. The AE 405, OE 407, RME 410, RPE 415, and HMMF 420 may be a collection of software modules, logic, and/or program code that enables the computer device 105 to operate according to the various example embodiments discussed herein. Other application(s) 365 may be a collection of software modules, logic, and/or program code that enables the computer device 105 to perform various other functions of the computer device 105 (e.g., social networking, email, games, word processing, and the like). In some embodiments, each of the other application(s) 365 may include APIs and/or middleware that allow the AE 405, OE 407, RME 410, RPE 415, and HMMF 420 to access associated data/information.

Processor circuitry 315 is configured to carry out instructions of a computer program by performing the basic arithmetical, logical, and input/output operations of the system. The processor circuitry 315 may include one or more processors (e.g., a single-core processor, a dual-core processor, a triple-core processor, a quad-core processor, etc.), one or more microcontrollers, one or more DSPs, FPGAs (hardware accelerators), one or more graphics processing units (GPUs), etc. The processor circuitry 315 may perform the logical operations, arithmetic operations, data processing operations, and a variety of other functions for the computer device 105. To do so, the processor circuitry 315 may execute program code, logic, software modules, firmware, middleware, microcode, hardware description languages, and/or any other like set of instructions stored in the memory 320. The program code may be provided to processor circuitry 315 by memory 320 via bus 335, communications circuitry 305, NIC 325, or separate drive mechanism. On execution of the program code by the processor circuitry 315, the processor circuitry 315 may cause computer device 105 to perform the various operations and functions delineated by the program code, such as the various example embodiments discussed herein. In embodiments where processor circuitry 315 include (FPGA based) hardware accelerators as well as processor cores, the hardware accelerators (e.g., the FPGA cells) may be pre-configured (e.g., with appropriate bit streams) with the logic to perform some of the functions of AE 405, OE 407, RME 410, RPE 415, and HMMF 420, rendering engine 370, OS 360 and/or other applications 365 (in lieu of employment of programming instructions to be executed by the processor core(s)).

Figure 4:
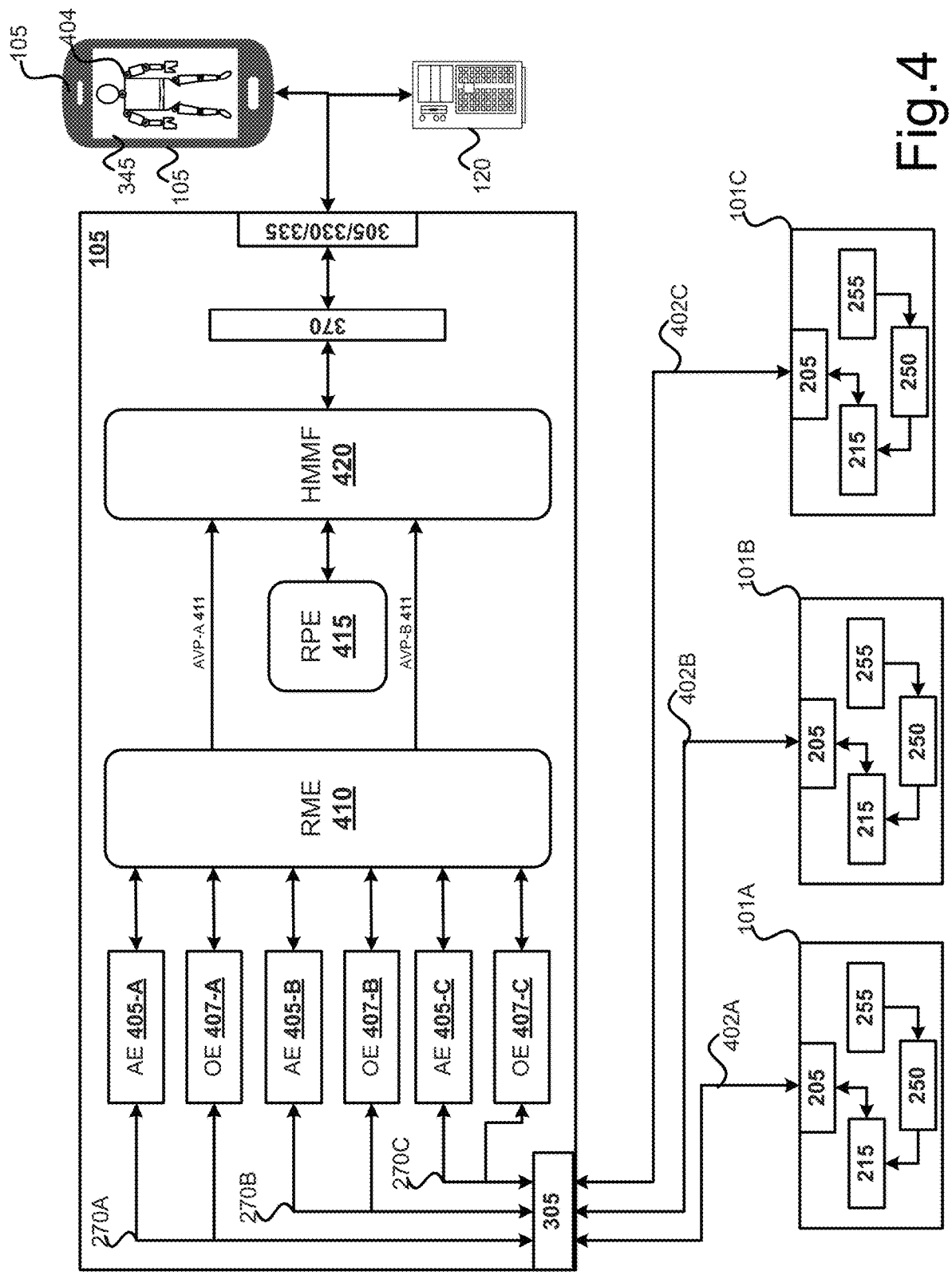
FIG. 4 illustrates example embodiments of logical components and interaction points between elements shown and described with regard to FIGS. 1-3.

Display module 340 is configured to provide generated content (e.g., avatar 404 discussed with regard to FIG. 4) to a display device for display/rendering (see e.g., display 345 shown and described with regard to FIG. 4). The display module 340 may be one or more software modules/logic that operate in conjunction with one or more hardware devices to provide data to a display device via the I/O interface 330. Depending on the type of display device used, the display module 340 may operate in accordance with one or more known display protocols, such as video graphics array (VGA) protocol, the digital visual interface (DVI) protocol, the high-definition multimedia interface (HDMI) specifications, the display pixel interface (DPI) protocol, and/or any other like standard that may define the criteria for transferring audio and/or video data to a display device. Furthermore, the display module 340 may operate in accordance with one or more remote display protocols, such as the wireless gigabit alliance (WiGiG) protocol, the remote desktop protocol (RDP), PC-over-IP (PCoIP) protocol, the high-definition experience (HDX) protocol, and/or other like remote display protocols. In such embodiments, the display module 340 may provide content to the display device via the NIC 325 or communications circuitry 305 rather than the I/O interface 330.

In some embodiments the components of computer device 105 may be packaged together to form a single package, IC, or SoC. Additionally, although FIG. 3 illustrates various components of the computer device 105, in some embodiments, computer device 105 may include more or less components than those shown in FIG. 3.

FIG. 4 shows example logical components and interaction points between components/logic of the computer devices 101 and 105, and the other elements of arrangement 100 according to various embodiments. The elements shown by FIG. 4 may operate as follows.

First, computer device 105 may communicatively couple with the computer devices 101. In this regard, communications circuitry 305 may use an antenna element (not shown) to establish corresponding radio links 402A, 402B, and 402C with respective communications circuitries 205 via associated antenna elements (not shown). The radio links 402 (also referred to as "channels 402", etc.) may be established in accordance with one or more wireless protocols discussed previously. As a user of the computer devices 101 performs a biomechanical motion, the sensor(s) 255 in each of the computer devices 101A-C may capture and record corresponding sensor data 270, which may be passed to a sensor hub 250 for processing. Each sensor hub 250 may pass the processed sensor data 270 to respective processor circuitries 215, which may then be passed to respective communications circuitries 205. Each of the communications circuitries 205 may perform various radio control functions to communicate the sensor data 270 to computer device 105 over corresponding radio links 402A-C. In some embodiments, the sensor data 270 may be stored or buffered in memory 220 prior to, or after being communicated to computer device 105 (not shown by FIG. 4). In some embodiments, the processor circuitry 215 may instruct or control the communications circuitry 205 to transmit the sensor data on a periodic basis, or based on whether certain triggers/conditions/thresholds have been met. Once received by communications circuitry 305, the sensor data 270 may be passed to corresponding AEs 405 and OEs 407. In FIG. 4, the sensor data 270A may have been captured, stored/recorded, and provided by the computer device 101A, the sensor data 270B may have been captured, stored/recorded, and provided by the computer device 101B, and the sensor data 270C may have been captured, stored/recorded, and provided by the computer device 101C.

AE 405A, AE 405B, and AE 405C (collectively referred to as "AEs 405" or "AE 405") may obtain sensor data 270A, sensor data 270B, and sensor data 270C (collectively referred to as "sensor data 270") captured by corresponding computer devices 101A-C, and may determine wrist accelerations and/or a torso acceleration based on based on the sensor data 270. For example, the AE 405A may determine/identify acceleration data of the right wrist from an acceleration component of the sensor data 270A, AE 405B may determine/identify acceleration data of the left wrist from an acceleration component of the sensor data 270B, and the AE 405C may determine/identify acceleration data of the torso from an acceleration component of the sensor data 270C. In some cases, the acceleration measurements may be influenced by gravity. In order to account for gravitational acceleration, each of the AEs 405 may subtract a gravity vector (e.g., 9.8 m/s$^2$ pointing towards the earth/ground) from the acceleration component to obtain a linear acceleration of the torso and wrists caused only by user 104 motion. In addition, the acceleration measurements may be measured in a local frame of reference (e.g., local to computer device 101 measuring the acceleration). In order to mitigate such issues, each of the AEs 405 may apply a reverse rotation operation to the accelerometer components (e.g., by multiplying the acceleration vector by a reverse rotation matrix, and the like) to obtain accelerometer data in the global coordinate system 505 (discussed infra). After the acceleration data is determined for the right wrist, left wrist, and torso, the acceleration data may be provided to the RME 415 discussed infra.

OE 407A, OE 407B, and OE 407C (collectively referred to as "OEs 407" or "OE 407") may obtain sensor data 270 captured by corresponding computer devices 101A-C, and may determine a torso orientation and/or wrist orientations based on the sensor data 270. For example, the OE 407A may determine/identify orientation data of the right wrist from a gyroscope component of the sensor data 270A, the OE 407B may determine/identify orientation data of the left wrist from a gyroscope component of the sensor data 270B, and the OE 407C may determine/identify orientation data of the torso from a gyroscope component of the sensor data 270C.

To determine the orientations of the right wrist, left wrist, and torso, in embodiments the OEs 407A-C may integrate a corresponding gyroscope component of the sensor data 270A-C (e.g., perform an integral operation on the angular velocity measured by the gyroscopes) to obtain a first orientation data. In some cases, the first orientation data may be accurate over short time periods, but may drift over longer periods of time. Second orientation data may be obtained from the acceleration component or a combination of the acceleration and magnetization components of the sensor data 270, which may be less accurate than the first orientation data but drift less over longer periods of time. The second orientation data may be used to mitigate errors associated with the drift of the first orientation data. In various embodiments, the OEs 407 may combine the first orientation data with the second orientation data. In embodiments, the OEs 407 may combine the aforementioned orientation data using a complementary filter. The complementary filter may include high pass filter circuitry that may receive the first orientation data, low pass filter circuitry that may receive the second orientation data, and adder or summation circuitry to combine the outputs of the high pass filter circuitry and the low pass filter circuitry. In other embodiments, rather than using low pass filter circuitry and high pass filter circuitry, the OEs 407 may use software logic to simulate the low pass filter circuitry and high pass filter circuitry. In some embodiments, the OEs 407 may determine weighted averages of the first orientation data and/or the second orientation data using, for example, a recursive function with inputs such as raw sensor data 270, sampling rate, delay times, etc.

Figure 5:
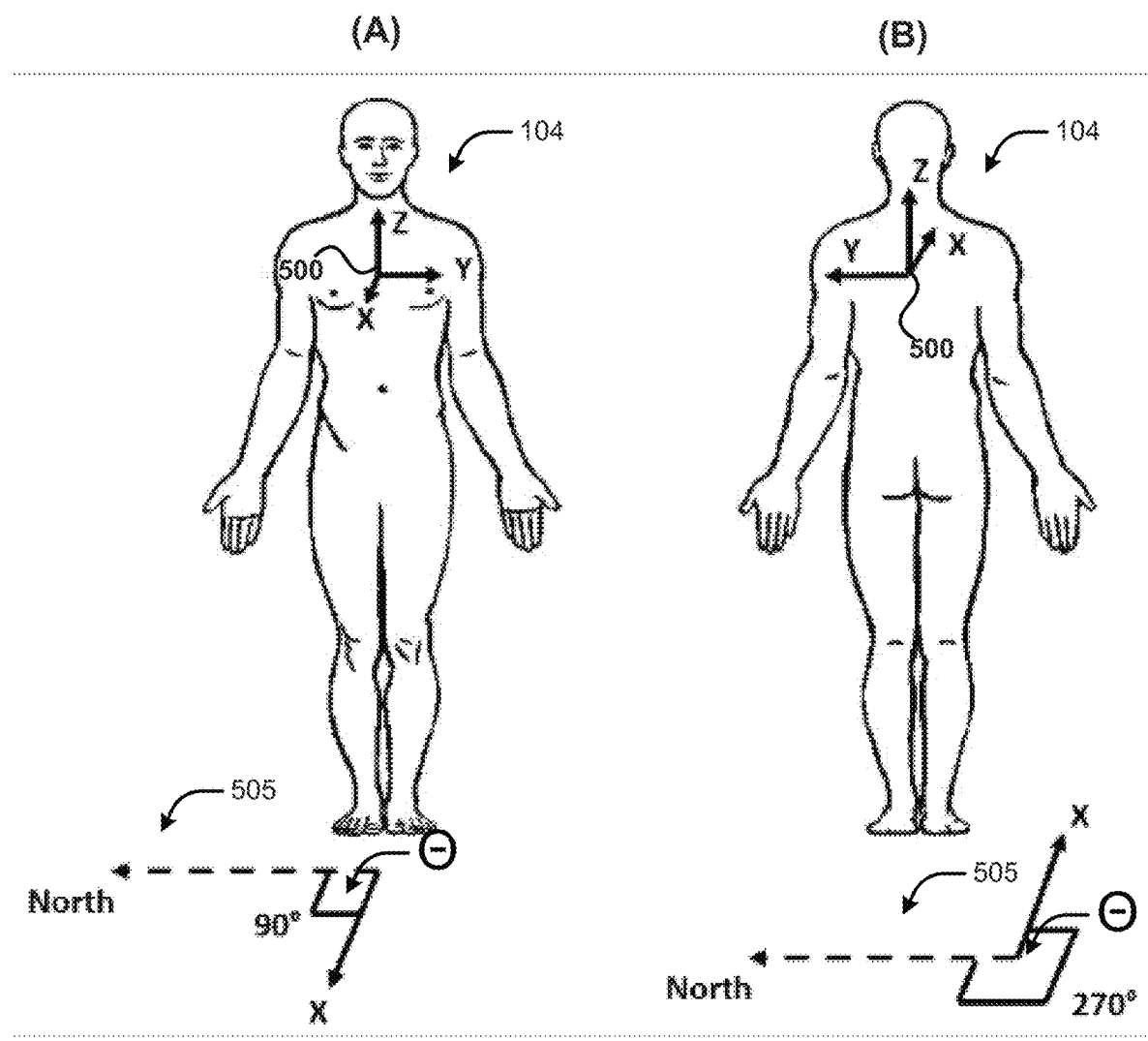
FIG. 5 illustrates an example a Torso Coordinate System (TCS) and Global Coordinate System (GSC) in accordance with various embodiments.

With regard the OE 407C, the orientation determined by the OE 407C may be a facing direction of the torso. In embodiments, a Torso Coordinate System (TCS) 500 may be defined as the frame of reference attached to the torso of user 104, which is shown by FIG. 5. As shown by FIG. 5, the TCS 500 may include an X-axis that points towards front portion of the user 104, a Y-axis that points towards a left side of the user 104, and a Z-axis that points towards a top portion of the user 104. The origin point of the TCS 500 may be located on the chest of the user 104, for example where the computer device 101C is located on the torso. In embodiments, a Global Coordinate System (GCS) 500 may also be defined, which includes an X-axis that points North, a Y-axis that points West, and a Z-axis that points up (not shown by FIG. 5). In embodiments, the GCS 505 does not change regardless of the biomechanical motions performed by the user 104, while the TCS 500 may change as the user 104 performs biomechanical motions. In addition, a facing direction theta ($\Phi$) may be defined as the angular difference from North to the X direction in TCS 500 in the counter-clockwise direction. For example, in FIG. 5, the facing directions $\Phi$ of (A) and portion (B) are 90° and 270°, respectively. After the orientation data is determined for the right wrist, left wrist, and torso, the orientation data may be provided to the RME 410.

Referring back to FIG. 4, the RME 410 may obtain the accelerometer data and orientation data from the AEs 405 and OEs 407, respectively, and determine a relative acceleration of the right elbow (RARE) based on the right wrist acceleration and the torso orientation, and/or a relative acceleration of the left elbow (RALE) based on the left wrist acceleration and the torso orientation. Because the computer device 101C may capture sensor data 270C based on torso movements and the computer devices 101A-B may capture sensor data 270A-B that is influenced by both the wrists and torso movements, the RME 410 extracts or separates the arm motions from the motion that includes both the arm and torso movements. In embodiments, the RME 410 decouples the wrist sensor measurements from the torso sensor measurement to obtain a motion of the wrist relative to the torso (also referred to as a "relative motion of the wrist" or the like). In embodiments, a mathematical model may fuse the measurements measured by the computer devices 101, which may then be used to separate the arm motions from the torso motions (separation of the arm and torso movements may be referred to as "tracking arm motions relative to the torso"). For example, equation 1 may represent the location of each arm at time t in the GCS 505.

$$L_{w|G}(t)=L_{e|G}(t)+L_{we|G}(t) \qquad \text{[Equation 1]}$$

In equation 1, $L_{w|G}(t)$ is the position/location of the wrist in the GCS 505 at time t, $L_{e|G}(t)$ is the position/location of the elbow (either the left or right elbow) in the GCS 505 at time t, and the $L_{we|G}(t)$ is a forearm position/location vector (e.g., a length or distance from the elbow to the wrist) in the GCS 505 at time t. The position/location of the elbow in the GCS 505 may be express by equation 2:

$$L_{e|G}(t)=R_\Theta(t)*L_{e|T}(t)+L_{T|G}(t) \qquad \text{[Equation 2]}$$

In equation 2, $L_{e|G}(t)$ is the position/location of the elbow (either the left or right elbow) in the GCS 505 at time t, $R_\Theta(t)$ is a rotation matrix related to the torso facing direction/angle $\Theta$ at time t, $L_{e|T}(t)$ is the position/location of the elbow in the TCS 500 at time t, and $L_{T|G}(t)$ is a position/location offset from the GCS 505 to the TCS 500 at time t. The position/location offset may be the position/location of the torso in the GCS 505, and in some embodiments, the position/location offset may be a constant value. Combining equations 1 and 2 may yield equation 3:

$$L_{w|G}(t)=R_\Theta(t) \cdot L_{e|T}(t)+L_{T|G}(t)+L_{we|G}(t) \qquad \text{[Equation 3]}$$

The computer device 101C may provide information for determining $R_\Theta(t)$ and $L_{T|G}(t)$, and the computer devices 101A-B may provide information for determining $L_{w|G}(t)$ and $L_{we|G}(t)$. In embodiments, the RME 410 may determine values for the elbow in the TCS 500 (e.g., $L_{e|T}(t)$) and the values for the wrist position/location in the TCS 500 (e.g., $L_{w|T}(t)$). For example, taking the second derivative of equation 3 may yield a motion equation, which may be expressed as equation 4:

$$A_{w|G}(t) - A_{T|G}(t) - A_{we|G}(t) = R_\Theta(t) \cdot A_{e|T}(t) + 2 \cdot R'_\Theta(t) \cdot V_{e|T}(t) + R''_\Theta(t) \cdot L_{e|T}(t)$$ [Equation 4]

In equation 4, $A_{w|G}(t)$ is the acceleration of the wrist in the GCS 505 at time t, $A_{e|T}(t)$ is the acceleration of the elbow in the TCS 500 at time t, $A_{we|G}(t)$ is a forearm acceleration vector in the GCS 505 at time t, $V_{e|T}(t)$ is a velocity of the elbow in the TCS 500 at time t, and $A_{T|G}(t)$ is an acceleration offset from the GCS 505 to the TCS 500 at time t. The acceleration offset may be the acceleration of the torso in the GCS 505, and in some embodiments, the acceleration offset may be a constant value. In addition, $R'_\Theta(t)$ and $R''_\Theta(t)$ are the first and second derivatives of the rotation matrix $R_\Theta(t)$ related to the facing angle $\Theta$ at time t.

In embodiments, the $A_{w|G}(t)$ and the $A_{T|G}(t)$ may be obtained from the AE 405A-C. $A_{we|G}(t)$ be the second derivative of $L_{we|G}(t)$, and because the forearm is a rigid body, this value may be derived from the orientation data obtained from OE 407A-B. The $R_\Theta(t)$, $R'_\Theta(t)$, and $R''_\Theta(t)$ may be derived from the facing direction $\Theta$ obtained from OE 407C. The unknown values from equation 4 include the relative acceleration of the elbow $A_{e|T}(t)$, elbow velocity $V_{e|T}(t)$, and position/location of the elbow $L_{e|T}(t)$ with respect to the torso. However, because these values are the integral/differential of one another, these values together may provide adequate information to determine the relative elbow position/location $L_{e|T}(t)$ itself. For example, once the wrist orientation is known, the wrist position/location can be inferred as a shift of the elbow position/location along a fixed direction of the computer device 101A-B on the wrist. In some cases, the elbow position/location and the wrist position/location may be a static shift of each other along the forearm in a positive or negative direction. The output AVP-A 411 and AVP-B 411 from the RME 410 may be values that represent the combined relative elbow acceleration, elbow velocity, and elbow position/location for the right arm and the left arm, respectively. The output of the RME 410 may be provided to the HMMF 420 (discussed infra) to determine a relative elbow/wrist position/location.

In embodiments, the RPE 415 may determine a right and left elbow state spaces (or "elbow search spaces") based on an elbow model. The elbow model may indicate relationships between wrist orientation, wrist location, and elbow location, and these relationships may be based on various arm postures. The arm postures may be based on the range of motion (RoM) of the arm joints and the degrees of freedom (DoF) of those joints. Typically, the human arm may have seven rotational DoF including three DoF for the shoulder, two DoF for the elbow, and two DoF for the wrist. The elbow model may be derived from the RoM and DoF. For example, for most individuals, the wrist can move to multiple positions/locations while preserving the same orientation when the elbow moves. In addition, since the forearm's ability to twist is limited, the wrist orientation may also be limited when the elbow remains static. Furthermore, the elbow may only move in a sphere around the shoulder. This suggests that for a given wrist orientation, the possible space of wrist positions/locations may be restricted. The wrist state space (or "wrist search space") will also vary across wrist orientations, for example, some wrist orientations may allow the wrist to move to more positions/locations than other wrist orientations. The term "search space" or "state space" as used herein refers to a set or domain to be searched, which may be an infinite set or may include data in a finite data structure. In the context of the present disclosure, an elbow search space may refer to a suitable data structure comprising a set of points of all possible elbow positions/locations given a set of constraints and/or conditions, and a wrist search space may refer to a suitable data structure comprising a set of points of all possible wrist positions/locations given a set of constraints and/or conditions.

Based on the elbow model, the RPE 415 may generate an elbow state space by mapping each computer device 101A-B orientation to a point in a wrist point cloud and a point in an elbow point cloud. In embodiments, the shoulder and elbow DoFs may be used to derive the elbow point cloud. This is because the computer devices 101A-B are worn on the wrist or on the forearm near the wrist, and therefore, the two wrist DoF are not manifested in the sensor data 270A-B. In embodiments, for each wrist orientation, the RPE 415 may determine all combinations of the shoulder and elbow DoF within a RoM that can generate an orientation according to equation 5:

$$R_w = h(\theta_1, \theta_2, \theta_3, \theta_4, \theta_5)$$ [Equation 5]

In equation 5, $\theta_1$, $\theta_2$, $\theta_3$, $\theta_4$, and $\theta_5$ are the five shoulder and elbow DoF, where $\theta_1$ is a should flexion/extension DoF, $\theta_2$ is a shoulder abduction/adduction DoF, $\theta_3$ is a shoulder inter/external rotation, $\theta_4$ is an elbow flexion/extension DoF, and $\theta_5$ is an elbow pronation/supination DoF; h is a rotational transform function; and $R_w$ is a rotation matrix for the wrist. Each DoF combination may be mapped to an elbow position/location according to equation 6:

$$L_{e|T} = f(\theta_1, \theta_2) = l_u((\cos \theta_2)(\sin \theta_1)(\sin \theta_1) - (\cos \theta_1)(\cos \theta_2))$$ [Equation 6]

In equation 6, $l_u$ is a known length of the upper arm (e.g., a length or distance between the elbow and shoulder), $L_{e|T}$ is the position/location of the elbow in the TCS 500, and f is a Denavit-Hartenberg transformation function. In addition, the RPE 415 may determine a mapping from $R_w$ to possible wrist positions/locations because for each $R_w$, possible wrist positions/locations are a shift of possible elbow positions/locations along the forearm, which may be expressed by equation 7:

$$L_{we} = R_w \begin{pmatrix} l_f \\ 0 \\ 0 \end{pmatrix}$$ [Equation 7]

In equation 7, $L_w$ may be a forearm position/location vector (e.g., a length or distance from the elbow to the wrist) similar to the $L_{we|G}(t)$ discussed previously with regard to equation 2, and $l_f$ is a known length of the forearm (e.g., a length or distance between the elbow and wrist). Using equations 5-7, the RPE 415 may obtain a mapping of wrist orientations $R_w$ to all possible elbow position/locations. Table 1 shows example pseudo code for wrist orientation to point cloud mapping.

TABLE 1

1: ElbowPointCloud = Empty Dictionary
2: WristPointCloud = Empty Dictionary
3: for all $\{\theta_1, \theta_2, \theta_3, \theta_4,$ and $\theta_5\} \in$ RoM do
4: $L_e(t) = f(\theta_1, \theta_2)$ TABLE 1-continued 5: $R_w(t) = h(\theta_1, \theta_2, \theta_3, \theta_4, \text{ and } \theta_5)$ 6: $L_{we}(t) = R_w(t) \begin{pmatrix} l_f \\ 0 \\ 0 \end{pmatrix}$ 7: $L_w(t) = L_e(t) + L_{we}(t)$
8: ElbowPointCloud[$R_w(t)$].Add($L_e(t)$)
9: WristPointCloud[$R_w(t)$].Add($L_w(t)$)
10: end for Once the RPE 415 populates the elbow point cloud with all possible elbow points, and populates the wrist point cloud with all possible wrist points, the RPE 415 may pass the elbow point cloud and the wrist point cloud to the HMMF 420. The elbow point cloud populated with all possible elbow points may be the elbow state space and the wrist point cloud with all possible wrist points may be the wrist state space.

HMMF 420 may determine a relative position of the right elbow (RPRE) and/or a relative position of the left elbow (RPLE) based on the RARE and the RALE. Given the coupling of elbow acceleration/velocity/location discussed previously, and given the possible search space of the potential elbow locations, in various embodiments the HMMF 420 may estimate the elbow location across time using Hidden Markov Model (HMM) filtering. As discussed previously, the elbow may move in a sphere around the shoulder joint with a radius substantially equal to the upper arm length. In embodiments, the HMMF 420 may discretize a sphere into N grids, and combine two grids together to form a tuple. In such embodiments, the N*N number of tuples may serve as an MINI state space, and each state may include two grid locations for the elbow. In order to transition from a state A to a state B, the following constraints may be required: 1) a location in state A should be the same as the former location in state B (also referred to as a "continuity constraint"); 2) both locations in state A and state B should fall within the elbow search space range; and 3) the three locations A(1)→A(2)/B(1)→B(2) in state transition A→B should be indicative of an elbow location, elbow velocity, and elbow acceleration, and should fit the arm relative motion equation as well as possible. Based on these constraints, a transition probability may be determined based on how well the elbow location, elbow velocity, and elbow acceleration fits the motion equation (e.g., equation 4 discussed previously). For example, in various embodiments, the motion equation may be expressed as equations 8 and 9.

$M = A_{w|G}(t) - A_{T|G}(t) - A_{we|G}(t)$ [Equation 8]

$N = R_\Theta(t) \cdot A_{e|T}(t) + 2 \cdot R'_\Theta(t) \cdot V_{e|T}(t) + R''_\Theta(t) \cdot L_{e|T}(t)$ [Equation 9]

In equation 8, M may represent the coupled motion of wrist, elbow and torso accelerations, and in equation 9, N may represent the coupled motion of elbow acceleration/velocity/location from the state tuple N as discussed previously. The remaining values in equations 8 and 9 may be the same as discussed previously with regard to equation 4. In such embodiments, the transition probability may be a Gaussian probability distribution, which may be expressed as equation 10.

$P = \left(\frac{1}{\sqrt{2\pi}\,\sigma}\right) e^{-(M-N)^2/2\sigma^2}$ [Equation 10]

In equation 10, P is the transition probability and a is a standard deviation of an estimation error. In some embodiments, the transition probability may be set as a constant value and the initial distribution evenly. The transition probability may be based on how well the acceleration/velocity/location fits the motion equations 8 and 9. In such embodiments, at each time t, the HMMF 420 may determine a state having a greatest or largest probability within the state space, and may output/report this state as the relative right or left elbow position/location. In embodiments, the HMMF 420 may then determine the RPRE or RPLE by shifting the relative right or left elbow position/location along the forearm vector as discussed previously. The output of the HMMF 420 may be the positions/locations of the elbow joint and the positions/locations of the wrist joint for each arm relative to the torso, regardless how torso moves or rotates. The positions/locations of the elbow and wrist may be expressed as coordinates, for example ($X_e$, $Y_e$, $Z_e$) for the elbow positions/locations and ($X_w$, $Y_w$, $Z_w$) for the wrist positions/locations, and/or using some other suitable format.

Regardless of their format, the wrist and elbow positions/locations output by the HMMF 420 may be passed to application server 120 via NIC 325 and/or communications circuitry 305 for further analysis, and/or to rendering engine 370 for generating an avatar 404. Rendering engine 370 may be specifically designed hardware (e.g., hardware accelerators) or program code that operates in conjunction with one or more hardware devices (e.g., GPUs, etc.) to generate and output images/animations from models, scene files, and/or other like data structures. In embodiments, the rendering engine 370 may obtain the wrist and elbow positions/locations from the HMMF 420, and use the wrist and elbow positions/locations to alter or adjust an avatar model, scene file, and/or other like data structure, and generate an image/animation of avatar 404 based on the adjusted/altered model/scene file/data structure. Rendering engine technologies are generally well known, and a description of the functionality of the rendering engine 370 is omitted for brevity. In some embodiments, the rendering engine 370 may provide the avatar 404 to application server 120 via NIC 325 and/or communications circuitry 305, which may be used for further analysis. In embodiments, the computer device 105 may implement the display module 340 to provide the avatar 404 to display 345 via I/O interface 335, NIC 325 and/or communications circuitry 305 for rendering/display.

The display 345 may operate in conjunction with the display module 340 (shown and described with regard to FIG. 3) display or render the generated animation 460. Display 345 may be any type of output device that is capable of presenting information in a visual form based on received electrical signals. Display 345 may be a light-emitting diode (LED) display device, an organic LED (OLED) display device, a liquid crystal display (LCD) device, a quantum dot display device, a projector device, and/or any other like display device. Furthermore, in various embodiments, the display 345 may be a touchscreen input device wherein a user may provide one or more inputs to the computer device 105 through one or more gestures by touching the display 345 with a stylus/pen and/or one or more fingers. The aforementioned display device technologies are generally well known, and a description of the functionality of the display 345 is omitted for brevity.

Figure 6:
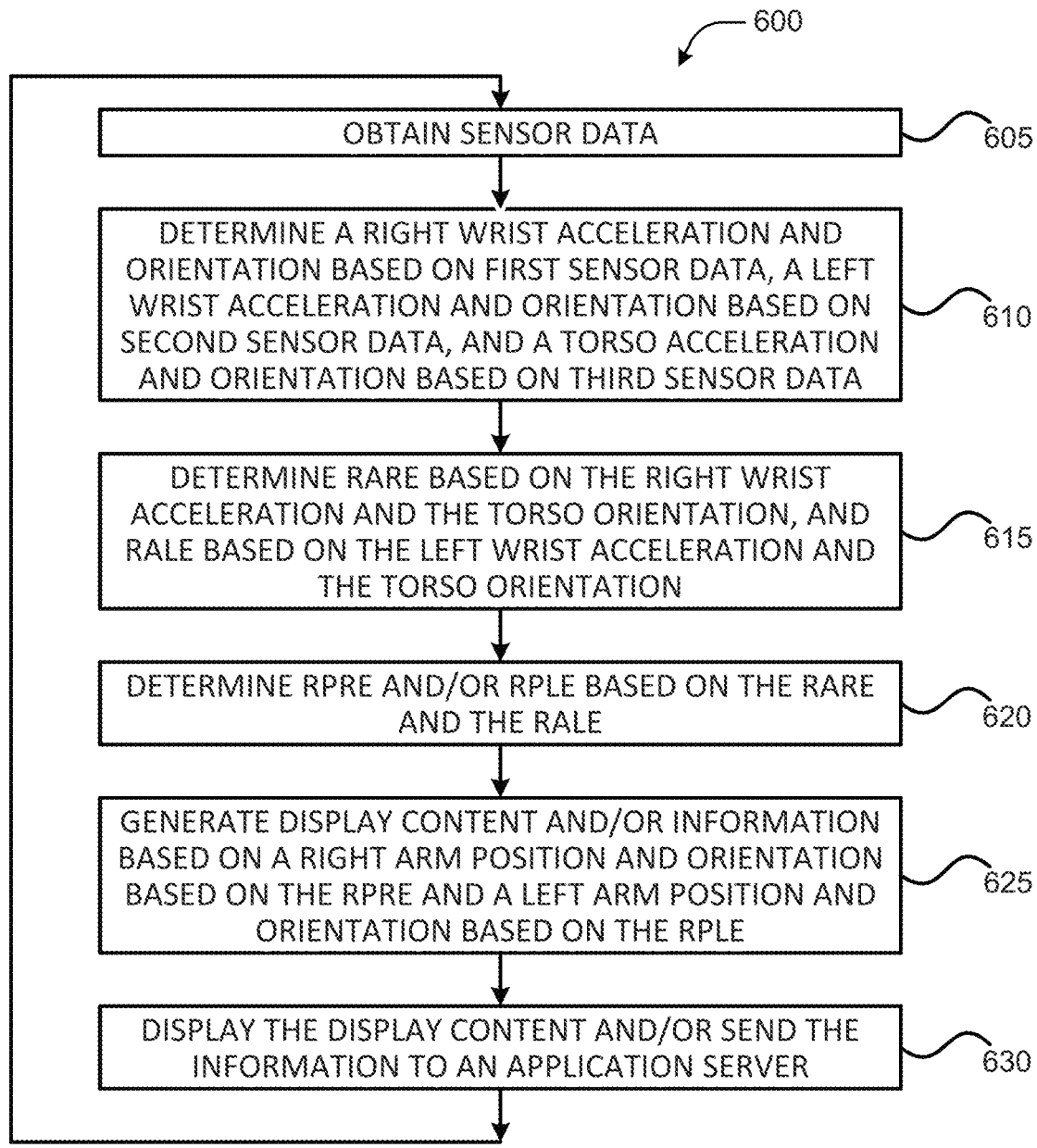
FIG. 6 illustrates a process for tracking body movements or biomechanical motions in accordance with various embodiments.

FIG. 6 illustrates process 600 for implementing the previously described embodiments. The process 600 may be implemented as a set of instructions (and/or bit streams) stored in a machine- or computer-readable storage medium, such as CRM 320 and/or computer-readable media 704 (described infra), and performed by a client system (with processor cores and/or hardware accelerators), such as the computer device 105 discussed previously. While particular examples and orders of operations are illustrated in FIG. 4, in various embodiments, these operations may be re-ordered, separated into additional operations, combined, or omitted altogether. In addition, the operations illustrated in each of FIG. 4 may be combined with operations described with regard to other example embodiments and/or one or more operations described with regard to the non-limiting examples provided herein.

Referring to FIG. 6, at operation 605, the communications circuitry 305 of the computer device 105 may receive sensor data 270A-C from a computer devices 101A-C. At operation 610, the computer device 105 implementing the AEs 405A-B may determine, in a global coordinate system (GCS), a right wrist acceleration based on sensor data 270A (also referred to as "first sensor data") and/or a left wrist acceleration based on sensor data 270B (also referred to as "second sensor data"). In embodiments, the computer device 105 may implement the AE 405C to determine, in the GCS, a torso acceleration based on sensor data 270C (also referred to as "third sensor data"). In embodiments, the determination of the right wrist, left wrist, and/or torso accelerations may be based on a reverse rotation of the acceleration component of the sensor data 270A-C and removal of a gravitational component from the acceleration component of the sensor data 270A-C. In embodiments, the AEs 405 may also determine right and left forearm accelerations based on the right and left wrist accelerations and a right and left forearm lengths, and determine a right and left elbow accelerations based on the right and left forearm accelerations.

At operation 610, the computer device 105 may also implement the OE 407C to determine a torso orientation based on the sensor data 270C. In embodiments, the computer device 105 may implement the OEs 407A-B to determine right and left wrist orientations based on the sensor data 270A-B, respectively. In embodiments, the OEs 407 may use a complimentary filter to determine the right wrist, the left wrist, and torso orientations. The complimentary filters may include a high pass filter and a low pass filter. In such embodiments, the OEs 407 may integrate the gyroscope component of the sensor data 270A-C and pass the integrated gyroscope data to the high pass filter. In addition, the OEs 407 may pass a combination of the acceleration and magnetization components of the sensor data 270A-C to the low pass filter. The OEs 407 may combine the output of the high pass filter and the output of the low pass filter to obtain the right wrist, left wrist, and torso orientations.

At operation 615, the computer device 105 may implement the RME 410 to determine the relative acceleration of a right elbow (RARE) based on the right wrist acceleration and the torso orientation and/or a relative acceleration of a left elbow (RALE) based on the left wrist acceleration and the torso orientation. At operation 620, the computer device 105 may implement an HMMF 420 to determine a relative position of the right elbow (RPRE) based on the RARE and/or a relative position of the left elbow (RPLE) based on the RALE.

In embodiments, the computer device 105 may implement the RPE 415 to identify a right elbow search space and a left elbow search space based on an elbow model. The RPE 415 may also determine a relative right elbow state (RRES) based on the right wrist acceleration and the right forearm acceleration, and determine a relative left elbow state (RLES) based on the left wrist acceleration and the left elbow acceleration. The RRES may correspond to a point within the right elbow search space, and the RLES corresponds to a point within the left elbow search space.

In embodiments, the computer device 105 may implement the HMMF 420 to identify a right elbow state space comprising a plurality of RRESs within the right elbow search space, and identify a left elbow state space comprising a plurality of RLESs within the left elbow search space. The HMMF 420 may determine a right elbow motion based on the right wrist acceleration and the right forearm acceleration, and determine a left elbow motion based on the left wrist acceleration and the left forearm acceleration. In embodiments, at operation 620 the HMMF 420 may determine the RPRE to be an RRES of the plurality of RRESs having a greatest value within a right elbow probability distribution, and determine the RPLE to be an RLES of the plurality of RLESs having a greatest value within a left elbow probability distribution. Each value in the right elbow probability distribution may be based on the right elbow motion and a corresponding RRES of the plurality of RRESs. Additionally, each value in the left elbow probability distribution is based on the left elbow motion and a corresponding RLES of the plurality of RLESs.

At operation 625, the computer device 105 may implement a rendering engine 370 to generate display content (e.g., an avatar 404, display text, and/or other like representation(s)) based on (or including) a right arm position and orientation based on the RPRE and a left arm position and orientation based on the RPLE. At operation 630, the computer device 105 may implement a display module 340 to provide, via the I/O interface 330, the generated display content for display on the display device 345. Additionally or alternatively, at operation 625, the computer device 105 may implement the processor circuitry 315 and HMMF 420 to generate information indicative or representative of the right arm position and orientation based on the RPRE and the left arm position and orientation based on the RPLE. In such embodiments, at operation 630 the computer device 105 may implement the communications circuitry 305 or NIC 325 to transmit/send the information to the application server 120. In some embodiments, transmission of the information to the application server 120 may be through a GW 103 or other like network element.

Figure 7:
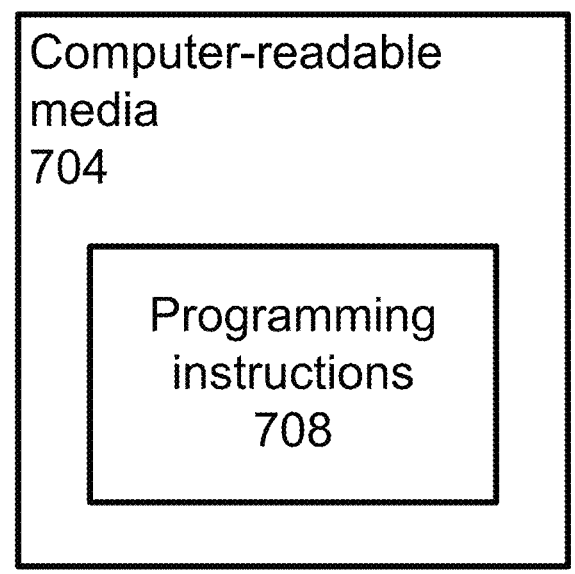
FIG. 7 illustrates an example computer-readable media, in accordance with various example embodiments.

FIG. 7 illustrates an example computer-readable media 704 that may be suitable for use to store instructions that cause an apparatus, in response to execution of the instructions by the apparatus, to practice selected aspects of the present disclosure. In some embodiments, the computer-readable media 704 may be non-transitory. In some embodiments, computer-readable media 704 may correspond to CRM 320 and/or any other computer-readable media discussed herein. As shown, computer-readable storage medium 704 may include programming instructions 708. Programming instructions 708 may be configured to enable a device, for example, computer device 105 or some other suitable device, in response to execution of the programming instructions 708, to implement (aspects of) any of the methods or elements described throughout this disclosure related to generating and displaying user interfaces to create and manage optimal day routes for users. In some embodiments, programming instructions 708 may be disposed on computer-readable media 704 that is transitory in nature, such as signals.

Any combination of one or more computer-usable or computer-readable media may be utilized. The computer-usable or computer-readable media may be, for example, but not limited to, an electronic, magnetic, optical, electromagnetic, infrared, or semiconductor system, apparatus, device, or propagation medium. More specific examples (a non-exhaustive list) of the computer-readable media would include the following: an electrical connection having one or more wires, a portable computer diskette, a hard disk, RAM, ROM, an erasable programmable read-only memory (for example, EPROM, EEPROM, or Flash memory), an optical fiber, a portable compact disc read-only memory (CD-ROM), an optical storage device, a transmission media such as those supporting the Internet or an intranet, or a magnetic storage device. Note that the computer-usable or computer-readable media could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable media may be any medium that can contain, store, communicate, propagate, or transport the program for use by or in connection with the instruction execution system, apparatus, or device. The computer-usable media may include a propagated data signal with the computer-usable program code embodied therewith, either in baseband or as part of a carrier wave. The computer-usable program code may be transmitted using any appropriate medium, including but not limited to wireless, wireline, optical fiber cable, radio frequency, and the like.

Computer program code for carrying out operations of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present disclosure is described with reference to flowchart illustrations or block diagrams of methods, apparatus (systems) and computer program products according to embodiments of the disclosure. It will be understood that each block of the flowchart illustrations or block diagrams, and combinations of blocks in the flowchart illustrations or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means that implement the function/act specified in the flowchart or block diagram block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide processes for implementing the functions/acts specified in the flowchart or block diagram block or blocks.

Some non-limiting examples are provided below.

Example 1 may include an apparatus comprising: an acceleration engine (AE) to determine, in a global coordinate system (GCS), a right wrist acceleration based on first sensor data, a left wrist acceleration based on second sensor data, and a torso acceleration based on third sensor data; an orientation engine (OE) to determine, in the GCS, a right wrist orientation based on the first sensor data, a left wrist orientation based on the second sensor data, and a torso orientation based on the third sensor data; a relative motion engine (RME) to determine a relative acceleration of a right elbow (RARE) based on the right wrist acceleration, the right wrist orientation, the torso acceleration, and the torso orientation, and/or a relative acceleration of a left elbow (RALE) based on the left wrist acceleration, the left wrist orientation, the torso acceleration, and the torso orientation; and a hidden Markov Model filter (HMMF) to determine a relative position of the right elbow (RPRE) or a relative position of the left elbow (RPLE) based on the RARE or the RALE, respectively.

Example 2 may include the apparatus of example 1 and/or some other examples herein, wherein each of the first sensor data, the second sensor data, and the third sensor data comprise a corresponding acceleration component, an orientation component, and a magnetization component, and wherein the OE is to: determine, using a complementary filter, the right wrist orientation based on the orientation component of the first sensor data and a combination of the acceleration component of the first sensor data and the magnetization component of the first sensor data; determine, using the complementary filter, the left wrist orientation based on the orientation component of the second sensor data and a combination of the acceleration component of the second sensor data and the magnetization component of the second sensor data; and determine, using the complementary filter, the torso orientation based on the orientation component of the third sensor data and a combination of the acceleration component of the third sensor data and the magnetization component of the third sensor data.

Example 3 may include the apparatus of example 1 or 2 and/or some other examples herein, wherein the AE is to: determine the right wrist acceleration in the GCS based on a reverse rotation of the acceleration component of the first sensor data and removal of a gravitational component from the acceleration component of the first sensor data; determine the left wrist acceleration in the GCS based on a reverse rotation of the acceleration component of the second sensor data and removal of a gravitational component from the acceleration component of the second sensor data; and determine the acceleration of the torso in the GCS based on a reverse rotation of the acceleration component of the third sensor data and removal of a gravitational component from the acceleration component of the third sensor data.

Example 4 may include the apparatus of any one of examples 1-3 and/or some other examples herein, wherein the AE is to: determine a right forearm acceleration based on the right wrist acceleration and a right forearm length; determine a right elbow acceleration based on the right forearm acceleration; determine a left forearm acceleration based on the left wrist acceleration and a left forearm length; and determine a left elbow acceleration based on the left forearm acceleration.

Example 5 may include the apparatus of example 4 and/or some other examples herein, wherein the RME is further to: determine based on the right elbow acceleration in the GCS, the right elbow orientation in the GCS, the torso acceleration in the GCS, and the torso orientation in the GCS, a relative right elbow acceleration in a torso coordinate system (TCS), a relative right elbow velocity in the TCS, and a relative right elbow location in the TCS; and determine, based on the left elbow acceleration in the GCS, the left elbow orientation in the GCS, the torso acceleration in the GCS, and the torso orientation in the GCS, a relative left elbow acceleration in the TCS, a relative left elbow velocity in the TCS, and a relative left elbow location in the TCS.

Example 6 may include the apparatus of example 5 and/or some other examples herein, wherein the relative right elbow acceleration is an acceleration of the right elbow that is relative to the torso, the relative right elbow velocity is a velocity of the right elbow relative to the torso, and the relative right elbow location is a location of the right elbow relative to the torso; and wherein the relative left elbow acceleration is an acceleration of the left elbow that is relative to the torso, the relative left elbow velocity is a velocity of the left elbow relative to the torso, and the relative left elbow location is a location of the left elbow relative to the torso.

Example 7 may include the apparatus of example 6 and/or some other examples herein, further comprising: a relative position engine (RPE) to: identify a right elbow search space and a left elbow search space based on an elbow model; determine a relative right elbow state (RRES) based on the right wrist acceleration and the right forearm acceleration, wherein the RRES corresponds to a point within the right elbow search space; and determine a relative left elbow state (RLES) based on the left wrist acceleration and the left elbow acceleration, wherein the RLES corresponds to a point within the left elbow search space.

Example 8 may include the apparatus of example 7 and/or some other examples herein, wherein the HMMF is to: identify a right elbow state space comprising a plurality of RRESs within the right elbow search space; determine a right elbow motion based on the right wrist acceleration and the right forearm acceleration; determine the RPRE to be an RRES of the plurality of RRESs having a greatest value within a right elbow probability distribution, wherein each value in the right elbow probability distribution is based on the right elbow motion and a corresponding RRES of the plurality of RRESs.

Example 9 may include the apparatus of example 8 and/or some other examples herein, wherein the HMMF is to: identify a left elbow state space comprising a plurality of RLESs within the left elbow search space; determine a left elbow motion based on the left wrist acceleration and the left forearm acceleration; determine the RPLE to be an RLES of the plurality of RLESs having a greatest value within a left elbow probability distribution, wherein each value in the left elbow probability distribution is based on the left elbow motion and a corresponding RLES of the plurality of RLESs.

Example 10 may include the apparatus of example 1 or 9 and/or some other examples herein, further comprising: communications circuitry to obtain the first sensor data from a first inertial sensor unit (IMU), obtain the second sensor data from a second IMU, and obtain the third sensor data from a third IMU, wherein each of the first IMU, the second IMU, and the third IMU include a corresponding microelectromechanical system (MEMS) accelerometer, a MEMS gyroscope, and a MEMS magnetometer, and wherein the first IMU is coupled with the right wrist, the second IMU is coupled with the left wrist, and the third IMU is coupled with the torso.

Example 11 may include the apparatus of example 10 and/or some other examples herein, wherein: the HMMF is further to generate information indicative or representative of a right arm position and orientation based on the RPRE and indicative or representative of a left arm position and orientation based on the RPLE; and the communications circuitry is to send the information to an application server for analysis and/or processing.

Example 12 may include the apparatus of example 1 or 11 and/or some other examples herein, further comprising: a rendering engine to generate display content based on a right arm position and orientation that is based on the RPRE and a left arm position and orientation that is based on the RPLE; and a display module to provide the display content to a display device for display.

Example 13 may include the apparatus of example 12 and/or some other examples herein, wherein the display device is coupled with the apparatus via a wired connection or a wireless connection.

Example 14 may include the apparatus of examples 1-13 and/or some other examples herein, wherein the apparatus is implemented in a wearable computer device, a smartphone, a tablet personal computer (PC), a head-up display (HUD) device, a laptop PC, a desktop PC, or a server computer.

Example 15 may include one or more computer-readable media including instructions, which when executed by a computer device, causes the computer device to: determine, in a global coordinate system (GCS), a right wrist acceleration and right wrist orientation based on first sensor data, a left wrist acceleration and left wrist orientation based on second sensor data, and a torso acceleration and torso orientation based on third sensor data; determine a relative acceleration of a right elbow (RARE) based on the right wrist acceleration, the right wrist orientation, the torso acceleration, and the torso orientation, and a relative acceleration of a left elbow (RALE) based on the left wrist acceleration, the left wrist orientation, the torso acceleration, and the torso orientation; determine a relative position of the right elbow (RPRE) or a relative position of the left elbow (RPLE) based on the RARE and the RALE; and control transmission of information to an application server, wherein the information is representative of a right arm position and orientation based on the RPRE and a left arm position and orientation based on the RPLE, and/or control display of a representation of the right arm position and orientation and the left arm position and orientation. In embodiments, the one or more computer-readable media may be non-transitory computer-readable media.

Example 16 may include the one or more computer-readable media of example 15 and/or some other examples herein, wherein each of the first sensor data, the second sensor data, and the third sensor data comprise a corresponding acceleration component, an orientation component, and a magnetization component, and wherein execution of the instructions cause the computer device to: determine, using a complementary filter, the right wrist orientation based on a combination of the orientation component of the first sensor data with the acceleration component of the first sensor data and the magnetization component of the first sensor data; determine, using the complementary filter, the left wrist orientation based on a combination of the orientation component of the second sensor data with the acceleration component of the second sensor data and the magnetization component of the second sensor data; and determine, using the complementary filter, the torso orientation based on a combination of the orientation component of the third sensor data with the acceleration component of the third sensor data and the magnetization component of the third sensor data.

Example 17 may include the one or more computer-readable media of example 15 or 16 and/or some other examples herein, wherein execution of the instructions cause the computer device to: determine the right wrist acceleration in the GCS based on a reverse rotation of the acceleration component of the first sensor data and removal of a gravitational component from the acceleration component of the first sensor data; determine the left wrist acceleration in the GCS based on a reverse rotation of the acceleration component of the second sensor data and removal of a gravitational component from the acceleration component of the second sensor data; and determine the acceleration of the torso in the GCS based on a reverse rotation of the acceleration component of the third sensor data and removal of a gravitational component from the acceleration component of the third sensor data.

Example 18 may include the one or more computer-readable media of any one of examples 15-17 and/or some other examples herein, wherein execution of the instructions cause the computer device to: determine a right forearm acceleration based on the right wrist acceleration and a right forearm length; determine a right elbow acceleration based on the right forearm acceleration; determine a left forearm acceleration based on the left wrist acceleration and a left forearm length; and determine a left elbow acceleration based on the left forearm acceleration.

Example 19 may include the one or more computer-readable media of example 18 and/or some other examples herein, wherein execution of the instructions cause the computer device to: determine based on the right elbow acceleration in the GCS, the right elbow orientation in the GCS, the torso acceleration in the GCS, and the torso orientation in the GCS, a relative right elbow acceleration in a torso coordinate system (TCS), a relative right elbow velocity in the TCS, and a relative right elbow location in the TCS; determine, based on the left elbow acceleration in the GCS, the left elbow orientation in the GCS, the torso acceleration in the GCS, and the torso orientation in the GCS, a relative left elbow acceleration in the TCS, a relative left elbow velocity in the TCS, and a relative left elbow location in the TCS.

Example 20 may include the one or more computer-readable media of example 19 and/or some other examples herein, wherein: the relative right elbow acceleration is an acceleration of the right elbow that is relative to the torso, the relative right elbow velocity is a velocity of the right elbow relative to the torso, and the relative right elbow location is a location of the right elbow relative to the torso; and the relative left elbow acceleration is an acceleration of the left elbow that is relative to the torso, the relative left elbow velocity is a velocity of the left elbow relative to the torso, and the relative left elbow location is a location of the left elbow relative to the torso.

Example 21 may include the one or more computer-readable media of example 20 and/or some other examples herein, wherein execution of the instructions cause the computer device to: identify a right elbow search space and a left elbow search space based on an elbow model; determine a relative right elbow state (RRES) based on the right wrist acceleration and the right forearm acceleration, wherein the RRES corresponds to a point within the right elbow search space; and determine a relative left elbow state (RLES) based on the left wrist acceleration and the left elbow acceleration, wherein the RLES corresponds to a point within the left elbow search space.

Example 22 may include the one or more computer-readable media of example 21 and/or some other examples herein, wherein, to determine the RPRE, execution of the instructions cause the computer device to: identify a right elbow state space comprising a plurality of RRESs within the right elbow search space; determine a right elbow motion based on the right wrist acceleration and the right forearm acceleration; determine the RPRE to be an RRES of the plurality of RRESs having a greatest value within a right elbow probability distribution, wherein each value in the right elbow probability distribution is based on the right elbow motion and a corresponding RRES of the plurality of RRESs.

Example 23 may include the one or more computer-readable media of example 21 or 22 and/or some other examples herein, wherein, to determine the RPLE, execution of the instructions cause the computer device to: identify a left elbow state space comprising a plurality of RLESs within the left elbow search space; determine a left elbow motion based on the left wrist acceleration and the left forearm acceleration; determine the RPLE to be an RLES of the plurality of RLESs having a greatest value within a left elbow probability distribution, wherein each value in the left elbow probability distribution is based on the left elbow motion and a corresponding RLES of the plurality of RLESs.

Example 24 may include the one or more computer-readable media of example 15 and/or some other examples herein, wherein execution of the instructions cause the computer device to: obtain the first sensor data from a first inertial sensor unit (IMU), obtain the second sensor data from a second IMU, and obtain the third sensor data from a third IMU, wherein each of the first IMU, the second IMU, and the third IMU include a corresponding microelectromechanical system (MEMS) accelerometer, a MEMS gyroscope, and a MEMS magnetometer, and wherein the first IMU is coupled with the right wrist, the second IMU is coupled with the left wrist, and the third IMU is coupled with the torso.

Example 25 may include the one or more computer-readable media of examples 15-24 and/or some other examples herein, wherein the apparatus is implemented in a wearable computer device, a smartphone, a tablet personal computer (PC), a head-up display (HUD) device, a laptop PC, a desktop PC, or a server computer.

Example 26 may include a method for tracking biomechanical motions, the method comprising: determining, by a computer device, a right wrist acceleration and orientation based on first sensor data, a left wrist acceleration and orientation based on second sensor data, and a torso acceleration and orientation based on third sensor data; determining, by a computer device, the right wrist acceleration, the left wrist acceleration, and the torso acceleration in a global coordinate system (GCS); determining, by the computer device, a relative acceleration of a right elbow (RARE) based on the right wrist and the torso's acceleration and orientation, and a relative acceleration of a left elbow (RALE) based on the left wrist and the torso's acceleration and orientation; determining, by the computer device, a relative position of the right elbow (RPRE) based on the RARE and a relative position of the left elbow (RPLE) based on the RALE; generating, by the computer device, display content based on the RPRE, the RPLE, and the torso orientation, wherein the display content includes a right arm position and orientation based on the RPRE, a left arm position and orientation based on the RPLE, and faces a direction based on the torso orientation; and providing, by the computer device, the display content to a display device for display.

Example 27 may include the method of example 26 and/or some other examples herein, wherein each of the first sensor data, the second sensor data, and the third sensor data comprise a corresponding acceleration component, an orientation component, and a magnetization component, and wherein the method further comprises: determining, by the computer device, using a complementary filter, the right wrist orientation based on a combination of the orientation component of the first sensor data with the acceleration component of the first sensor data and the magnetization component of the first sensor data; determining, by the computer device, using the complementary filter, the left wrist orientation based on a combination of the orientation component of the second sensor data with the acceleration component of the second sensor data and the magnetization component of the second sensor data; and determining, by the computer device, using the complementary filter, the torso orientation based on a combination of the orientation component of the third sensor data with the acceleration component of the third sensor data and the magnetization component of the third sensor data.

Example 28 may include the method of example 26 or 27 and/or some other examples herein, further comprising: determining, by the computer device, the right wrist acceleration in the GCS based on a reverse rotation of the acceleration component of the first sensor data and removal of a gravitational component from the acceleration component of the first sensor data; determining, by the computer device, the left wrist acceleration in the GCS based on a reverse rotation of the acceleration component of the second sensor data and removal of a gravitational component from the acceleration component of the second sensor data; and determining, by the computer device, the acceleration of the torso in the GCS based on a reverse rotation of the acceleration component of the third sensor data and removal of a gravitational component from the acceleration component of the third sensor data.

Example 29 may include the method of any one of examples 26-28 and/or some other examples herein, further comprising: determining, by the computer device, a right forearm acceleration based on the right wrist acceleration and a right forearm length; determining, by the computer device, a right elbow acceleration based on the right forearm acceleration; determining, by the computer device, a left forearm acceleration based on the left wrist acceleration and a left forearm length; and determining, by the computer device, a left elbow acceleration based on the left forearm acceleration.

Example 30 may include the method of example 29 and/or some other examples herein, further comprising: determining, by the computer device, a relative right elbow acceleration in a torso coordinate system (TCS), a relative right elbow velocity in the TCS, and a relative right elbow location in the TCS, wherein determining the relative right elbow acceleration, the relative right elbow velocity, and the relative right elbow location is based on the right elbow acceleration in the GCS, the right elbow orientation in the GCS, the torso acceleration in the GCS, and the torso orientation in the GCS; and determining, by the computer device, a relative left elbow acceleration in a torso coordinate system (TCS), a relative left elbow velocity in the TCS, and a relative left elbow location in the TCS, wherein determining the relative left elbow acceleration, the relative left elbow velocity, and the relative left elbow location is based on the right elbow acceleration in the GCS, the left elbow orientation in the GCS, the torso acceleration in the GCS, and the torso orientation in the GCS.

Example 31 may include the method of example 30 and/or some other examples herein, wherein: the relative right elbow acceleration is an acceleration of the right elbow that is relative to the torso, the relative right elbow velocity is a velocity of the right elbow relative to the torso, and the relative right elbow location is a location of the right elbow relative to the torso; and the relative left elbow acceleration is an acceleration of the left elbow that is relative to the torso, the relative left elbow velocity is a velocity of the left elbow relative to the torso, and the relative left elbow location is a location of the left elbow relative to the torso.

Example 32 may include the method of example 30 or 31 and/or some other examples herein, further comprising: identifying, by the computer device, a right elbow search space and a left elbow search space based on an elbow model; determining, by the computer device, a relative right elbow state (RRES) based on the right wrist acceleration and the right forearm acceleration, wherein the RRES corresponds to a point within the right elbow search space; and determining, by the computer device, a relative left elbow state (RLES) based on the left wrist acceleration and the left elbow acceleration, wherein the RLES corresponds to a point within the left elbow search space.

Example 33 may include the method of example 32 and/or some other examples herein, wherein determining the RPRE comprises: identifying, by the computer device, a right elbow state space comprising a plurality of RRESs within the right elbow search space; determining, by the computer device, a right elbow motion based on the right wrist acceleration and the right forearm acceleration; determining, by the computer device, the RPRE to be an RRES of the plurality of RRESs having a greatest value within a right elbow probability distribution, wherein each value in the right elbow probability distribution is based on the right elbow motion and a corresponding RRES of the plurality of RRESs.

Example 34 may include the method of example 32 or 33 and/or some other examples herein, wherein determining the RPLE comprises: identifying, by the computer device, a left elbow state space comprising a plurality of RLESs within the left elbow search space; determining, by the computer device, a left elbow motion based on the left wrist acceleration and the left forearm acceleration; determining, by the computer device, the RPLE to be an RLES of the plurality of RLESs having a greatest value within a left elbow probability distribution, wherein each value in the left elbow probability distribution is based on the left elbow motion and a corresponding RLES of the plurality of RLESs.

Example 35 may include the method of example 26 and/or some other examples herein, further comprising: obtaining, by the computer device, the first sensor data from a first inertial sensor unit (IMU), obtain the second sensor data from a second IMU, and obtain the third sensor data from a third IMU, wherein each of the first IMU, the second IMU, and the third IMU include a corresponding microelectromechanical system (MEMS) accelerometer, a MEMS gyroscope, and a MEMS magnetometer, and wherein the first IMU is coupled with the right wrist, the second IMU is coupled with the left wrist, and the third IMU is coupled with the torso.

Example 36 may include the method of examples 26-35 and/or some other examples herein, wherein the method is performed by an apparatus, wherein the apparatus is implemented in a wearable computer device, a smartphone, a tablet personal computer (PC), a head-up display (HUD) device, a laptop PC, a desktop PC, or a server computer.

Example 36.5 may include one or more computer-readable media including instructions, which when executed by one or more processors of a computer device, causes the computer device to perform the method of examples 26-36 and/or some other examples herein. In embodiments, the one or more computer-readable media may be non-transitory computer-readable media.

Example 37 may include an apparatus comprising: acceleration determination means for determining, in a global coordinate system (GCS), a right wrist acceleration based on first sensor data, a left wrist acceleration based on second sensor data, and a torso acceleration based on third sensor data; orientation determination means for determining, in the GCS, a right wrist orientation based on the first sensor data, a left wrist orientation based on the second sensor data, and a torso orientation based on the third sensor data; relative motion determination means for determining a relative acceleration of a right elbow (RARE) based on the right wrist acceleration, the right wrist orientation, the torso acceleration, and the torso orientation, and/or a relative acceleration of a left elbow (RALE) based on the left wrist acceleration, the left wrist orientation, the torso acceleration, and the torso orientation; and hidden Markov Model filtering means for determining a relative position of the right elbow (RPRE) or a relative position of the left elbow (RPLE) based on the RARE and the RALE.

Example 38 may include the apparatus of example 37 and/or some other examples herein, wherein each of the first sensor data, the second sensor data, and the third sensor data comprise a corresponding acceleration component, an orientation component, and a magnetization component, and wherein the orientation determination means is further for determining: determining, using a complementary filter, the right wrist orientation based on the orientation component of the first sensor data and a combination of the acceleration component of the first sensor data and the magnetization component of the first sensor data; determining, using the complementary filter, the left wrist orientation based on the orientation component of the second sensor data and a combination of the acceleration component of the second sensor data and the magnetization component of the second sensor data; and determining, using the complementary filter, the torso orientation based on the orientation component of the third sensor data and a combination of the acceleration component of the third sensor data and the magnetization component of the third sensor data.

Example 39 may include the apparatus of example 37 or 38 and/or some other examples herein, wherein the acceleration determination means is further for: determining the right wrist acceleration in the GCS based on a reverse rotation of the acceleration component of the first sensor data and removal of a gravitational component from the acceleration component of the first sensor data; determining the left wrist acceleration in the GCS based on a reverse rotation of the acceleration component of the second sensor data and removal of a gravitational component from the acceleration component of the second sensor data; and determining the acceleration of the torso in the GCS based on a reverse rotation of the acceleration component of the third sensor data and removal of a gravitational component from the acceleration component of the third sensor data.

Example 40 may include the apparatus of any one of examples 37-39 and/or some other examples herein, wherein the acceleration determination means is further for: determining a right forearm acceleration based on the right wrist acceleration and a right forearm length; determining a right elbow acceleration based on the right forearm acceleration; determining a left forearm acceleration based on the left wrist acceleration and a left forearm length; and determining a left elbow acceleration based on the left forearm acceleration.

Example 41 may include the apparatus of example 40 and/or some other examples herein, wherein the relative motion determination means is further for: determining based on the right elbow acceleration in the GCS, the right elbow orientation in the GCS, the torso acceleration in the GCS, and the torso orientation in the GCS, a relative right elbow acceleration in a torso coordinate system (TCS), a relative right elbow velocity in the TCS, and a relative right elbow location in the TCS; and determining, based on the left elbow acceleration in the GCS, the left elbow orientation in the GCS, the torso acceleration in the GCS, and the torso orientation in the GCS, a relative left elbow acceleration in the TCS, a relative left elbow velocity in the TCS, and a relative left elbow location in the TCS.

Example 42 may include the apparatus of example 41 and/or some other examples herein, wherein: the relative right elbow acceleration is an acceleration of the right elbow that is relative to the torso, the relative right elbow velocity is a velocity of the right elbow relative to the torso, and the relative right elbow location is a location of the right elbow relative to the torso; and the relative left elbow acceleration is an acceleration of the left elbow that is relative to the torso, the relative left elbow velocity is a velocity of the left elbow relative to the torso, and the relative left elbow location is a location of the left elbow relative to the torso.

Example 43 may include the apparatus of example 42 and/or some other examples herein, further comprising relative position determination means for: identifying a right elbow search space and a left elbow search space based on an elbow model; determining a relative right elbow state (RRES) based on the right wrist acceleration and the right forearm acceleration, wherein the RRES corresponds to a point within the right elbow search space; and determining a relative left elbow state (RLES) based on the left wrist acceleration and the left elbow acceleration, wherein the RLES corresponds to a point within the left elbow search space.

Example 44 may include the apparatus of example 43 and/or some other examples herein, wherein the hidden Markov Model filtering means is further for: identifying a right elbow state space comprising a plurality of RRESs within the right elbow search space; determining a right elbow motion based on the right wrist acceleration and the right forearm acceleration; determining the RPRE to be an RRES of the plurality of RRESs having a greatest value within a right elbow probability distribution, wherein each value in the right elbow probability distribution is based on the right elbow motion and a corresponding RRES of the plurality of RRESs.

Example 45 may include the apparatus of example 44 and/or some other examples herein, wherein the hidden Markov Model filtering means is further for: identifying a left elbow state space comprising a plurality of RLESs within the left elbow search space; determining a left elbow motion based on the left wrist acceleration and the left forearm acceleration; determining the RPLE to be an RLES of the plurality of RLESs having a greatest value within a left elbow probability distribution, wherein each value in the left elbow probability distribution is based on the left elbow motion and a corresponding RLES of the plurality of RLESs.

Example 46 may include the apparatus of example 37 or 45 and/or some other examples herein, further comprising: communications means for obtaining the first sensor data from a first inertial sensor unit (IMU), obtain the second sensor data from a second IMU, and obtain the third sensor data from a third IMU, wherein each of the first IMU, the second IMU, and the third IMU include a corresponding microelectromechanical system (MEMS) accelerometer, a MEMS gyroscope, and a MEMS magnetometer, and wherein the first IMU is coupled with the right wrist, the second IMU is coupled with the left wrist, and the third IMU is coupled with the torso.

Example 47 may include the apparatus of example 46 and/or some other examples herein, wherein: the hidden Markov Model filtering means is further for generating information indicative or representative of a right arm position and orientation based on the RPRE and indicative or representative of a left arm position and orientation based on the RPLE; and the communications means is further for sending the information to an application server for analysis and/or processing.

Example 48 may include the apparatus of example 37 or 47 and/or some other examples herein, further comprising: rendering means for generating display content based on a right arm position and orientation that is based on the RPRE and a left arm position and orientation that is based on the RPLE; and display means for obtaining the generated display content and for providing the generated display content to a display device for display.

Example 49 may include the apparatus of example 48 and/or some other examples herein, wherein the display device is coupled with the apparatus via a wired connection or a wireless connection.

Example 50 may include the apparatus of examples 37-49 and/or some other examples herein, wherein the apparatus is implemented in a wearable computer device, a smartphone, a tablet personal computer (PC), a head-up display (HUD) device, a laptop PC, a desktop PC, or a server computer.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein, limited only by the claims.

The invention claimed is:

1. An apparatus comprising:
   an acceleration engine (AE) arranged to determine, in a global coordinate system (GCS), a right wrist acceleration based on first sensor data, a left wrist acceleration based on second sensor data, and a torso acceleration based on third sensor data;
   an orientation engine (OE) arranged to determine, in the GCS, a right wrist orientation based on the first sensor data, a left wrist orientation based on the second sensor data, and a torso orientation based on the third sensor data;
   a relative motion engine (RME) arranged to;
   determine a relative acceleration of a right elbow (RARE) based on the right wrist acceleration, the right wrist orientation, the torso acceleration, and the torso orientation, the RARE being acceleration of the right elbow relative to an acceleration of the torso, and
   determine a relative acceleration of a left elbow (RALE) based on the left wrist acceleration, the left wrist orientation, the torso acceleration, and the torso orientation, the RALE being acceleration of the left elbow relative to the acceleration of the torso; and
   a hidden Markov Model filter (HMMF) arranged to determine a relative position of the right elbow (RPRE) based on the determined RARE and a relative position of the left elbow (RPLE) based on the determined RALE.

2. The apparatus of claim 1, wherein the AE is arranged to:
   determine the right wrist acceleration in the GCS based on a reverse rotation of an acceleration component of the first sensor data and removal of a gravitational component from the acceleration component of the first sensor data;
   determine the left wrist acceleration in the GCS based on a reverse rotation of an acceleration component of the second sensor data and removal of a gravitational component from the acceleration component of the second sensor data; and
   determine the acceleration of the torso in the GCS based on a reverse rotation of an acceleration component of the third sensor data and removal of a gravitational component from the acceleration component of the third sensor data.

3. The apparatus of claim 1, wherein the AE is arranged to:
   determine a right forearm acceleration based on the right wrist acceleration and a right forearm length;
   determine a right elbow acceleration based on the right forearm acceleration;
   determine a left forearm acceleration based on the left wrist acceleration and a left forearm length; and
   determine a left elbow acceleration based on the left forearm acceleration.

4. The apparatus of claim 3, wherein the RME is arranged further to:
   determine, based on the right elbow acceleration in the GCS, the right elbow orientation in the GCS, the torso acceleration in the GCS, and the torso orientation in the GCS, the RARE in a torso coordinate system (TCS), a relative right elbow velocity in the TCS, and a relative right elbow location in the TCS; and
   determine, based on the left elbow acceleration in the GCS, the left elbow orientation in the GCS, the torso acceleration in the GCS, and the torso orientation in the GCS, the RALE in the TCS, a relative left elbow velocity in the TCS, and a relative left elbow location in the TCS.

5. The apparatus of claim 4, wherein:
   the RARE is an acceleration of the right elbow that is relative to the torso,
   the relative right elbow velocity is a velocity of the right elbow relative to the torso,
   the relative right elbow location is a location of the right elbow relative to the torso,
   the RALE is an acceleration of the left elbow that is relative to the torso, the relative left elbow velocity is a velocity of the left elbow relative to the torso, and
the relative left elbow location is a location of the left elbow relative to the torso.

6. The apparatus of claim 4, further comprising:
a relative position engine (RPE) arranged to:
identify a right elbow search space (RESS) and a left elbow search space (LESS) based on an elbow model, the RESS including potential right elbow positions, and the LESS including potential left elbow positions;
determine a relative right elbow state (RRES) based on the right wrist acceleration and the right elbow acceleration, wherein the RRES corresponds to a point within the RESS; and
determine a relative left elbow state (RLES) based on the left wrist acceleration and the left elbow acceleration, wherein the RLES corresponds to a point within the LESS.

7. The apparatus of claim 1, further comprising:
communications circuitry arranged to obtain the first sensor data from a first inertial measurement unit (IMU), obtain the second sensor data from a second IMU, and obtain the third sensor data from a third IMU, wherein each of the first IMU, the second IMU, and the third IMU include a corresponding microelectromechanical system (MEMS) accelerometer, a MEMS gyroscope, and a MEMS magnetometer, and
wherein the first IMU is coupled with the right wrist, the second IMU is coupled with the left wrist, and the third IMU is coupled with the torso.

8. The apparatus of claim 1, wherein the apparatus is implemented in a wearable computer device, a smartphone, a tablet personal computer (PC), a head-up display (HUD) device, a laptop PC, a desktop PC, or a server computer.

9. One or more non-transitory computer-readable media (NTCRM) comprising instructions, wherein execution of the instructions by one or more processors is to cause a computer device to:
determine, in a global coordinate system (GCS), a right wrist acceleration and right wrist orientation based on first sensor data, a left wrist acceleration and left wrist orientation based on second sensor data, and a torso acceleration and torso orientation based on third sensor data;
determine a relative acceleration of a right elbow (RARE) based on the right wrist acceleration, the right wrist orientation, the torso acceleration, and the torso orientation, and a relative acceleration of a left elbow (RALE) based on the left wrist acceleration, the left wrist orientation, the torso acceleration, and the torso orientation;
determine a relative position of the right elbow (RPRE) and a relative position of the left elbow (RPLE) based on the RARE and the RALE, respectively; and
control transmission of information to an application server, wherein the information is representative of a right arm position and orientation based on the RPRE and a left arm position and orientation based on the RPLE.

10. The one or more NTCRM of claim 9, wherein execution of the instructions is to cause the computer device to:
determine the right wrist acceleration in the GCS based on a reverse rotation of an acceleration component of the first sensor data and removal of a gravitational component from the acceleration component of the first sensor data;
determine the left wrist acceleration in the GCS based on a reverse rotation of an acceleration component of the second sensor data and removal of a gravitational component from the acceleration component of the second sensor data; and
determine the acceleration of the torso in the GCS based on a reverse rotation of an acceleration component of the third sensor data and removal of a gravitational component from the acceleration component of the third sensor data.

11. The one or more NTCRM of claim 9, wherein execution of the instructions is to cause the computer device to:
determine a right forearm acceleration based on the right wrist acceleration and a right forearm length;
determine a right elbow acceleration based on the right forearm acceleration;
determine a left forearm acceleration based on the left wrist acceleration and a left forearm length; and
determine a left elbow acceleration based on the left forearm acceleration.

12. The one or more NTCRM of claim 11, wherein execution of the instructions is to cause the computer device to:
determine each of the RARE, a relative right elbow velocity, and a relative right elbow location in a torso coordinate system (TCS), based on the right elbow acceleration in the GCS, the right elbow orientation in the GCS, the torso acceleration in the GCS, and the torso orientation in the GCS;
determine the RALE, a relative left elbow velocity, and a relative left elbow location in the TCS based on the left elbow acceleration in the GCS, the left elbow orientation in the GCS, the torso acceleration in the GCS, and the torso orientation in the GCS.

13. The one or more NTCRM of claim 12, wherein:
the RARE is an acceleration of the right elbow that is relative to the torso, the relative right elbow velocity is a velocity of the right elbow relative to the torso, and the relative right elbow location is a location of the right elbow relative to the torso; and
the RALE is an acceleration of the left elbow that is relative to the torso, the relative left elbow velocity is a velocity of the left elbow relative to the torso, and the relative left elbow location is a location of the left elbow relative to the torso.

14. The one or more NTCRM of claim 13, wherein execution of the instructions is to cause the computer device to:
identify a right elbow search space (RESS) and a left elbow search space (LESS) based on an elbow model, the RESS including potential right elbow positions, and the LESS including potential left elbow positions;
determine a relative right elbow state (RRES) based on the right wrist acceleration and the right elbow acceleration, wherein the RRES corresponds to a point within the RESS; and
determine a relative left elbow state (RLES) based on the left wrist acceleration and the left elbow acceleration, wherein the RLES corresponds to a point within the LESS.

15. The one or more NTCRM of claim 14, wherein, to determine the RPRE, execution of the instructions is to cause the computer device to:

identify a right elbow state space comprising a plurality of RRESs within the RESS;

determine a right elbow motion based on the right wrist acceleration and the right forearm acceleration;

determine the RPRE to be an RRES of the plurality of RRESs having a greatest value within a right elbow probability distribution, wherein each value in the right elbow probability distribution is based on the right elbow motion and a corresponding RRES of the plurality of RRESs.

16. The one or more NTCRM of claim 14, wherein, to determine the RPLE, execution of the instructions is to cause the computer device to:

identify a left elbow state space comprising a plurality of RLESs within the LESS;

determine a left elbow motion based on the left wrist acceleration and the left forearm acceleration;

determine the RPLE to be an RLES of the plurality of RLESs having a greatest value within a left elbow probability distribution, wherein each value in the left elbow probability distribution is based on the left elbow motion and a corresponding RLES of the plurality of RLESs.

17. A method for tracking biomechanical motions, the method comprising:

determining, by a computer device, a right wrist acceleration and orientation based on first sensor data, a left wrist acceleration and orientation based on second sensor data, and a torso acceleration and orientation based on third sensor data;

determining, by a computer device, the right wrist acceleration, the left wrist acceleration, and the torso acceleration in a global coordinate system (GCS);

determining, by the computer device, a relative acceleration of a right elbow (RARE) based on the right wrist and the torso's acceleration and orientation, and a relative acceleration of a left elbow (RALE) based on the left wrist and the torso's acceleration and orientation;

determining, by the computer device, a relative position of the right elbow (RPRE) based on the RARE and a relative position of the left elbow (RPLE) based on the RALE;

generating, by the computer device, display content based on the RPRE, the RPLE, and the torso orientation, wherein the display content includes a right arm position and orientation based on the RPRE, a left arm position and orientation based on the RPLE, and faces a direction based on the torso orientation; and providing, by the computer device, the display content to a display device for display.

18. The method of claim 17, further comprising:

determining, by the computer device, the right wrist acceleration in the GCS based on a reverse rotation of an acceleration component of the first sensor data and removal of a gravitational component from the acceleration component of the first sensor data;

determining, by the computer device, the left wrist acceleration in the GCS based on a reverse rotation of an acceleration component of the second sensor data and removal of a gravitational component from the acceleration component of the second sensor data; and determining, by the computer device, the acceleration of the torso in the GCS based on a reverse rotation of an acceleration component of the third sensor data and removal of a gravitational component from the acceleration component of the third sensor data.

19. The method of claim 17, further comprising:

determining, by the computer device, a right forearm acceleration based on the right wrist acceleration and a right forearm length;

determining, by the computer device, a right elbow acceleration based on the right forearm acceleration;

determining, by the computer device, a left forearm acceleration based on the left wrist acceleration and a left forearm length; and determining, by the computer device, a left elbow acceleration based on the left forearm acceleration.

20. The method of claim 19, further comprising:

determining, by the computer device, a relative right elbow acceleration in a torso coordinate system (TCS), a relative right elbow velocity in the TCS, and a relative right elbow location in the TCS, wherein determining the relative right elbow acceleration, the relative right elbow velocity, and the relative right elbow location is based on the right elbow acceleration in the GCS, the right elbow orientation in the GCS, the torso acceleration in the GCS, and the torso orientation in the GCS; and determining, by the computer device, a relative left elbow acceleration in a torso coordinate system (TCS), a relative left elbow velocity in the TCS, and a relative left elbow location in the TCS, wherein determining the relative left elbow acceleration, the relative left elbow velocity, and the relative left elbow location is based on the right elbow acceleration in the GCS, the left elbow orientation in the GCS, the torso acceleration in the GCS, and the torso orientation in the GCS.

21. The method of claim 20, wherein:

the relative right elbow acceleration is an acceleration of the right elbow that is relative to the torso, the relative right elbow velocity is a velocity of the right elbow relative to the torso, and the relative right elbow location is a location of the right elbow relative to the torso; and the relative left elbow acceleration is an acceleration of the left elbow that is relative to the torso, the relative left elbow velocity is a velocity of the left elbow relative to the torso, and the relative left elbow location is a location of the left elbow relative to the torso.

22. The method of claim 21, further comprising:

identifying, by the computer device, a right elbow search space (RESS) and a left elbow search space (LESS) based on an elbow model;

determining, by the computer device, a relative right elbow state (RRES) based on the right wrist acceleration and the right forearm acceleration, wherein the RRES corresponds to a point within the RESS; and determining, by the computer device, a relative left elbow state (RLES) based on the left wrist acceleration and the left elbow acceleration, wherein the RLES corresponds to a point within the LESS.

23. The method of claim 22, wherein determining the RPRE comprises:

identifying, by the computer device, a right elbow state space comprising a plurality of RRESs within the RESS;

determining, by the computer device, a right elbow motion based on the right wrist acceleration and the right forearm acceleration;

determining, by the computer device, the RPRE to be an RRES of the plurality of RRESs having a greatest value within a right elbow probability distribution, wherein each value in the right elbow probability distribution is based on the right elbow motion and a corresponding RRES of the plurality of RRESs.

24. The method of claim 22, wherein determining the RPLE comprises:
identifying, by the computer device, a left elbow state space comprising a plurality of RLESs within the LESS;
determining, by the computer device, a left elbow motion based on the left wrist acceleration and the left forearm acceleration;
determining, by the computer device, the RPLE to be an RLES of the plurality of RLESs having a greatest value within a left elbow probability distribution, wherein each value in the left elbow probability distribution is based on the left elbow motion and a corresponding RLES of the plurality of RLESs.

25. The method of claim 17, further comprising:
obtaining, by the computer device, the first sensor data from a first inertial measurement unit (IMU),
obtaining the second sensor data from a second IMU, and
obtaining the third sensor data from a third IMU,
wherein each of the first IMU, the second IMU, and the third IMU include a corresponding microelectromechanical system (MEMS) accelerometer, a MEMS gyroscope, and a MEMS magnetometer, and
wherein the first IMU is coupled with the right wrist, the second IMU is coupled with the left wrist, and the third IMU is coupled with the torso.

* * * * *

UNITED STATES PATENT AND TRADEMARK OFFICE
CERTIFICATE OF CORRECTION

PATENT NO. : 10,646,139 B2
APPLICATION NO. : 15/369614
DATED : May 12, 2020
INVENTOR(S) : Xue Yang et al.

Page 1 of 1

It is certified that error appears in the above-identified patent and that said Letters Patent is hereby corrected as shown below:

In the Claims

Column 34
Line 1, replace the ";" after "to" with a ":".

Signed and Sealed this
Twenty-first Day of July, 2020

Andrei Iancu
*Director of the United States Patent and Trademark Office*